US012577317B2

(12) United States Patent
Yu et al.

(10) Patent No.: US 12,577,317 B2
(45) Date of Patent: Mar. 17, 2026

(54) ANTI-CD5 ANTIBODY COMPOSITIONS AND USES THEREOF

(71) Applicant: CITY OF HOPE, Duarte, CA (US)

(72) Inventors: Hua Yu, Duarte, CA (US); Chunyan Zhang, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 544 days.

(21) Appl. No.: 18/022,460

(22) PCT Filed: Aug. 20, 2021

(86) PCT No.: PCT/US2021/047026
§ 371 (c)(1),
(2) Date: Feb. 21, 2023

(87) PCT Pub. No.: WO2022/040608
PCT Pub. Date: Feb. 24, 2022

(65) Prior Publication Data
US 2023/0340141 A1     Oct. 26, 2023

Related U.S. Application Data

(60) Provisional application No. 63/068,780, filed on Aug. 21, 2020.

(51) Int. Cl.
*C07K 16/28*        (2006.01)
*A61P 35/00*        (2006.01)

(52) U.S. Cl.
CPC .......... *C07K 16/2896* (2013.01); *A61P 35/00* (2018.01); *C07K 16/2818* (2013.01); *C07K 2317/24* (2013.01); *C07K 2317/55* (2013.01); *C07K 2317/565* (2013.01); *C07K 2317/567* (2013.01); *C07K 2317/622* (2013.01)

(58) Field of Classification Search
None
See application file for complete search history.

(56) References Cited

U.S. PATENT DOCUMENTS

2008/0254027 A1 * 10/2008 Bernett ................... A61P 35/02
435/375

* cited by examiner

*Primary Examiner* — Daniel E Kolker
*Assistant Examiner* — James Ryland Melchior
(74) *Attorney, Agent, or Firm* — Mintz Levin Cohn Ferris Glovsky and Popeo PC

(57) ABSTRACT

Provided herein are, inter alia, antibodies (e.g., humanized antibodies, monoclonal antibodies) and antibody compositions (e.g., chimeric antigen receptors, bispecific antibodies) that are capable of binding CD5. The antibodies and antibody compositions provided herein include novel light and heavy chain domain CDRs and framework regions, and bind CD5 with high efficiency and specificity, thereby effectively targeting CD5 expressing cells. The antibodies provided herein may form part of recombinant proteins also referred to herein as antibody compositions (e.g., chimeric antigen receptors or bispecific antibodies) to be used, inter alia, for therapeutic cancer applications.

19 Claims, 15 Drawing Sheets

Specification includes a Sequence Listing.

SEQUENCE LISTING

<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 1

Glu Ser Val Asp Ser Tyr Gly Asn Ser Phe
1               5                   10

<210> SEQ ID NO 2
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 2

Leu Ala Ser
1

<210> SEQ ID NO 3

-continued

```
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Gln Gln Asn Asn Glu Asp Pro Tyr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 4

Gly Phe Asn Ile Lys Asp Ser Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 5

Ile Asp Pro Ala Asn Gly Asp Thr
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 6

Ala Arg Glu Tyr Arg Tyr Ala Met Asp Tyr
1               5                   10

<210> SEQ ID NO 7
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 7

Asn Ile Val Leu Thr Gln Ser Pro Ala Ser Leu Pro Val Ser Leu Gly
1               5                   10                  15

Gln Arg Ala Thr Ile Ser Cys Arg Ala Ser
            20                  25

<210> SEQ ID NO 8
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 8

Met His Trp Tyr Gln Gln Lys Pro Gly Gln Pro Pro Lys Leu Leu Ile
1               5                   10                  15
```

-continued

Tyr

<210> SEQ ID NO 9
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 9

Asn Leu Glu Ser Gly Val Pro Ala Arg Phe Ser Gly Ser Gly Ser Arg
1               5                   10                  15

Thr Asp Phe Ile Leu Thr Ile Asp Pro Val Glu Ala Asp Asp Ala Ala
            20                  25                  30

Thr Tyr Tyr Cys
        35

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 10

Phe Gly Gly Gly Thr Lys Leu Glu Ile Lys
1               5                   10

<210> SEQ ID NO 11
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 11

Glu Val Gln Leu Gln Glu Ser Gly Ala Glu Leu Val Lys Pro Gly Ala
1               5                   10                  15

Ser Val Lys Leu Ser Cys Thr Ala Ser
            20                  25

<210> SEQ ID NO 12
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 12

Met His Trp Val Lys Gln Arg Pro Glu Gln Gly Leu Glu Trp Ile Gly
1               5                   10                  15

Arg

<210> SEQ ID NO 13
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 13

Gln Tyr Asp Pro Lys Phe Gln Gly Lys Ala Thr Ile Thr Ala Asp Thr
1               5                   10                  15

Ser Ser Asn Thr Ala Tyr Leu Gln Leu Ser Gly Leu Thr Ser Glu Asp

-continued
_____

```
              20                  25                  30

Thr Ala Val Tyr Tyr Cys
        35

<210> SEQ ID NO 14
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 14

Trp Gly Gln Gly Thr Ser Val Thr Val Ser Ser
1               5                   10

<210> SEQ ID NO 15
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 15

Asn Ile Val Leu Thr Gln Ser Pro Ala Ser Leu Pro Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Ile Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Tyr Thr Phe Gly Gly Gly Thr Lys Leu Glu Ile Lys
            100                 105                 110

<210> SEQ ID NO 16
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 16

Glu Val Gln Leu Gln Glu Ser Gly Ala Glu Leu Val Lys Pro Gly Ala
1               5                   10                  15

Ser Val Lys Leu Ser Cys Thr Ala Ser Gly Phe Asn Ile Lys Asp Ser
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asp Thr Gln Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Gly Leu Thr Ser Glu Asp Thr Ala Val Tyr Tyr Cys
                85                  90                  95

Ala Arg Glu Tyr Arg Tyr Ala Met Asp Tyr Trp Gly Gln Gly Thr Ser
            100                 105                 110
```

-continued

```
Val Thr Val Ser Ser
        115

<210> SEQ ID NO 17
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 17
gaaagtgttg atagttatgg caatagtttt                                   30

<210> SEQ ID NO 18
<211> LENGTH: 9
<212> TYPE: DNA
<213> ORGANISM: Artificial Sequence
<220> FEATURE:
<223> OTHER INFORMATION: Synthetic polynucleotide

<400> SEQUENCE: 18 cttgcatcc                                                           9

<210> SEQ ID NO 19
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 19
cagcaaaata atgaggatcc ttacacg                                      27

<210> SEQ ID NO 20
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 20
ggcttcaaca ttaaagactc ctat                                         24

<210> SEQ ID NO 21
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 21
attgatcctg cgaatggtga tact                                         24

<210> SEQ ID NO 22
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 22
gctagagagt ataggtacgc tatggactac                                   30

<210> SEQ ID NO 23
<211> LENGTH: 78
```

```
<212> TYPE: DNA
<213> ORGANISM: Artificial Sequence
<220> FEATURE:
<223> OTHER INFORMATION: Synthetic polynucleotide

<400> SEQUENCE: 23
aacattgtgc tgacccaatc tccagcttct ttgcctgtgt ctctagggca gagggccacc      60
atatcctgca gagccagt                                                     78

<210> SEQ ID NO 24
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 24
atgcactggt accagcagaa accaggacag ccacccaaac tcctcatcta t               51

<210> SEQ ID NO 25
<211> LENGTH: 108
<212> TYPE: DNA
<213> ORGANISM: Artificial Sequence
<220> FEATURE:
<223> OTHER INFORMATION: Synthetic polynucleotide

<400> SEQUENCE: 25
aacctagaat ctggggtccc tgccaggttc agtggcagtg ggtctaggac agacttcatc      60
ctcaccattg atcctgtgga ggctgatgat gctgcaacct attactgt                   108

<210> SEQ ID NO 26
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 26
ttcggagggg ggaccaagct ggaaataaaa c                                     31

<210> SEQ ID NO 27
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 27
gaggtgcagc tgcaggagtc tggggcagag cttgtgaaac caggggcctc agtcaagttg      60
tcctgcacag cttct                                                       75

<210> SEQ ID NO 28
<211> LENGTH: 51
<212> TYPE: DNA
<213> ORGANISM: Artificial Sequence
<220> FEATURE:
<223> OTHER INFORMATION: Synthetic polynucleotide

<400> SEQUENCE: 28
atgcactggg tgaagcagag gcctgaacag ggcctggagt ggattggaag g               51

<210> SEQ ID NO 29
<211> LENGTH: 114
<212> TYPE: DNA
```

-continued

```
<213> ORGANISM: Artificial Sequence
<220> FEATURE:
<223> OTHER INFORMATION: Synthetic polynucleotide

<400> SEQUENCE: 29
caatatgacc cgaagttcca gggcaaggcc actataacag cagacacatc ctccaacaca      60
gcctacctgc agctcagcgg cctgacatct gaggacactg ccgtctatta ctgt          114

<210> SEQ ID NO 30
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 30
tggggtcaag gaacctcagt caccgtctcc tcag                                 34

<210> SEQ ID NO 31
<211> LENGTH: 334
<212> TYPE: DNA
<213> ORGANISM: Artificial Sequence
<220> FEATURE:
<223> OTHER INFORMATION: Synthetic polynucleotide

<400> SEQUENCE: 31
aacattgtgc tgacccaatc tccagcttct ttgcctgtgt ctctagggca gagggccacc      60
atatcctgca gagccagtga aagtgttgat agttatggca atagtttat gcactggtac      120 cagcagaaac caggacagcc acccaaactc ctcatctatc ttgcatccaa cctagaatct      180
ggggtccctg ccaggttcag tggcagtggg tctaggacag acttcatcct caccattgat      240
cctgtggagg ctgatgatgc tgcaacctat tactgtcagc aaaataatga ggatccttac      300
acgttcggag gggggaccaa gctggaaata aaac                                 334

<210> SEQ ID NO 32
<211> LENGTH: 352
<212> TYPE: DNA
<213> ORGANISM: Artificial Sequence
<220> FEATURE:
<223> OTHER INFORMATION: Synthetic polynucleotide

<400> SEQUENCE: 32
gaggtgcagc tgcaggagtc tggggcagag cttgtgaaac caggggcctc agtcaagttg      60
tcctgcacag cttctggctt caacattaaa gactcctata tgcactgggt gaagcagagg      120
cctgaacagg gcctggagtg gattggaagg attgatcctg cgaatggtga tactcaatat      180
gacccgaagt tccagggcaa ggccactata acagcagaca catcctccaa cacagcctac      240
ctgcagctca gcggcctgac atctgaggac actgccgtct attactgtgc tagagagtat      300
aggtacgcta tggactactg gggtcaagga acctcagtca ccgtctcctc ag             352
```

1

ANTI-CD5 ANTIBODY COMPOSITIONS AND USES THEREOF

CROSS-REFERENCES TO RELATED APPLICATIONS

This application is a national stage filing under U.S.C. 371 of international application PCT/US2021/047026, filed Aug. 20, 2021, which claims priority to U.S. Provisional Application No. 63/068,780, filed Aug. 21, 2020, the disclosures of which are incorporated herein in their entireties and for all purposes.

STATEMENT AS TO RIGHTS TO INVENTIONS MADE UNDER FEDERALLY SPONSORED RESEARCH AND DEVELOPMENT

This invention was made with government support under grant no. CA122976, awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 048440-771001WO_SequenceListing_ST25.txt, created on Aug. 19, 2021, 12,288 bytes, machine format IBM-PC, MS-Windows operating system, is hereby incorporated by reference in its entirety for all purposes.

BACKGROUND

CD5 has been shown to activate STAT3 in both tumor-associated B and T cells, leading to immune-suppression. There is a need in the art for potent checkpoint inhibitors to activate T cells and B cells and elicit anti-cancer immune responses in patients in need thereof. The compositions and methods provided herein address these and other needs in the art.

BRIEF SUMMARY

In an aspect is provided an anti-CD5 antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

In an aspect is provided a pharmaceutical composition including a therapeutically effective amount of an antibody provided herein including embodiments thereof and a pharmaceutically acceptable excipient.

In an aspect is provided a method of treating cancer in a subject in need thereof, the method including administering to a subject a combined effective amount of an antibody provided herein including embodiments thereof and a PD-1 inhibitor, thereby treating cancer in the subject.

In an aspect is provided a recombinant protein including: (i) an antibody region including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6; and (ii) a transmembrane domain.

In an aspect is provided an isolated nucleic acid encoding a recombinant protein provided herein including embodiments thereof.

In an aspect is provided a pharmaceutical composition including a therapeutically effective amount of a recombinant protein provided herein including embodiments thereof and a pharmaceutically acceptable excipient.

In an aspect is provided a method of treating cancer in a subject in need thereof, the method including administering to a subject a therapeutically effective amount of a recombinant protein provided herein including embodiments thereof, thereby treating cancer in the subject.

In an aspect is provided a recombinant protein including: (i) a first antibody region capable of binding an effector cell ligand; and (ii) a second antibody region, including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6.

In an aspect is provided a pharmaceutical composition including a therapeutically effective amount of a recombinant protein provided herein including embodiments thereof and a pharmaceutically acceptable excipient.

In aspect is provided a method of treating cancer in a subject in need thereof, the method including administering to a subject a therapeutically effective amount of a recombinant protein provided herein including embodiments thereof, thereby treating cancer in the subject.

BRIEF DESCRIPTION OF THE DRAWINGS

FIG. 1A is a tumor growth curve showing inhibition of B16 tumor growth in Rag1−/− mice when CD5− B cells are included in the adoptively transferred T cells. Results shown are representative of two independent experiments (n=6). *P<0.05. FIG. 1B is a bar graph showing ELISA assessing IFN-γ production from mouse T cells co-cultured with CD5+ or CD5− splenic B cells in the presence of irradiated B16 tumor cells, means SEM (n=3). P<0.01. FIG. 1C shows bar graphs showing ELISA detecting IL-10 and IL-12 production from mouse dendritic cells co-cultured with CD5+ or CD5− splenic B cells in the presence of irradiated B16 tumor cells. Data represent means±SEM (n=3). P<0.01.

FIG. 2A is a fluorescence assisted cell sorting (FACS) plot showing single cell suspensions prepared from tumors in PyMT mice were analyzed by flow cytometry for CD5, PD1 expression and on CD8$^+$ T cells and Granzyme B producing in different subclasses of CD8$^+$ T cells. FIG. 2B is a bar graph showing statistical results of flow cytometry analyses showing Granzyme B+ cells frequencies in CD8+ T cells. FIG. 2C is a bar graph showing C57BU6 mouse CD8$^+$ T cells were either unstimulated (UT) or Incubated with coated anti-CD3 and soluble anti-CD8 antibody, the T cell co-stimulators, and IL2 (Tcc), or Tcc with CD5-blocking antibody or IgG control (Tcc+CD5 Ab, Tcc+IgG2a) for 48 hours. IFNy production was determined in supernatant from CD8$^+$ T cells cultured medium by ELISA. Data are shown as means±SEM (n=3). Data are shown as means±SEM (n=4). FIG. 2D is a bar graph showing mouse CD8$^+$ T cells from spleen were activated by anti-CD3/CD28 for two days, the activated CD8$^+$ T cells were co-cultured with irradiated tumor cells in the presence of isotype control or antibody as indicated for 48 h. IFN-γ production were determined in supernatant from co-cultured medium by ELISA. FIG. 2E is a bar graph showing mouse CD8$^+$ T cells from spleen were activated by anti-CD3/CD28 for two days, the activated CD8$^+$ T cells were co-cultured with irradiated tumor cells in the presence of isotype control or antibody as indicated for 48 h. Granzyme production were determined in supernatant from co-cultured medium by ELISA.

FIG. 3A is a fluorescence assisted cell sorting plot showing flow cytometric analysis of 9F2A11 or UCHT2 (commercially available through, for example, Biolegend) binding to CD5 on human T cells. FIG. 3B is a graph showing that bound 9F2A11 was detected using HRPconjugated anti-human Fab antibody and addition of chromogenic substrate (OD 450) on 96 well plates which were previously coated with 0.5 ug/well of recombinant human CD5. Each data point is the average of two replicates. Data are representative of three independent experiments.

FIG. 4A shows the light-chain variable (VL) nucleic acid sequence (SEQ ID NO:31) of 9F2A11 on top and the light-chain variable (VL) amino acid sequence (SEQ ID NO:15) of 9F2A11 on the bottom. FIG. 4B shows the heavy-chain variable (VH) nucleic acid sequence (SEQ ID NO:32) of 9F2A11 on top and the heavy-chain variable (VH) amino acid sequence (SEQ ID NO:16) of 9F2A11 on the bottom.

DETAILED DESCRIPTION

Figure 1A:
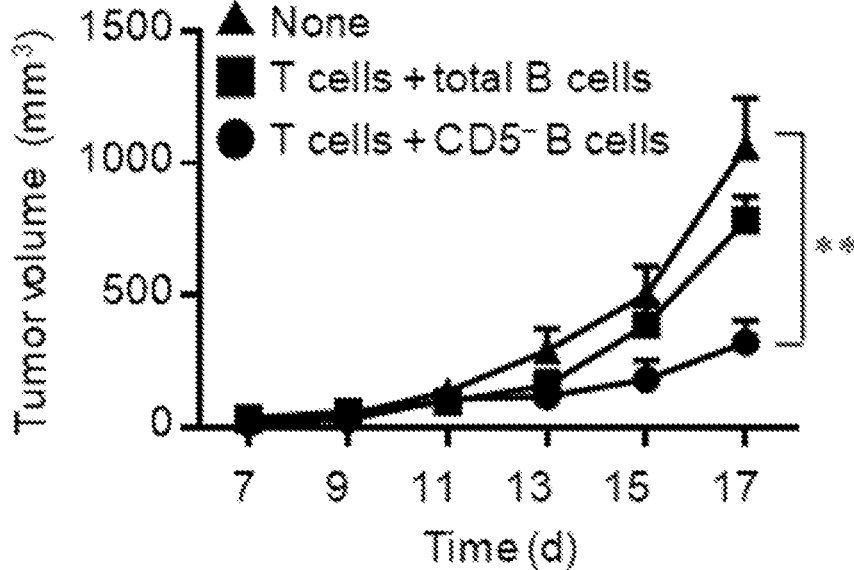
FIGS. 1A-1C present illustrative data showing that CD5+ B cells promoted B16 melanoma progression through T-cell suppression.
Figure 1B:
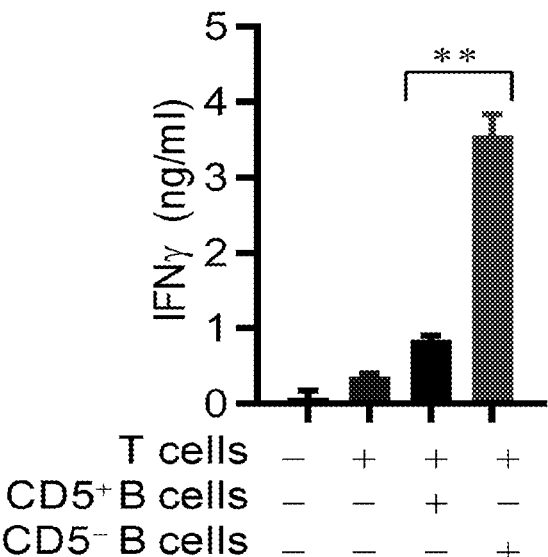
Figure 1C:
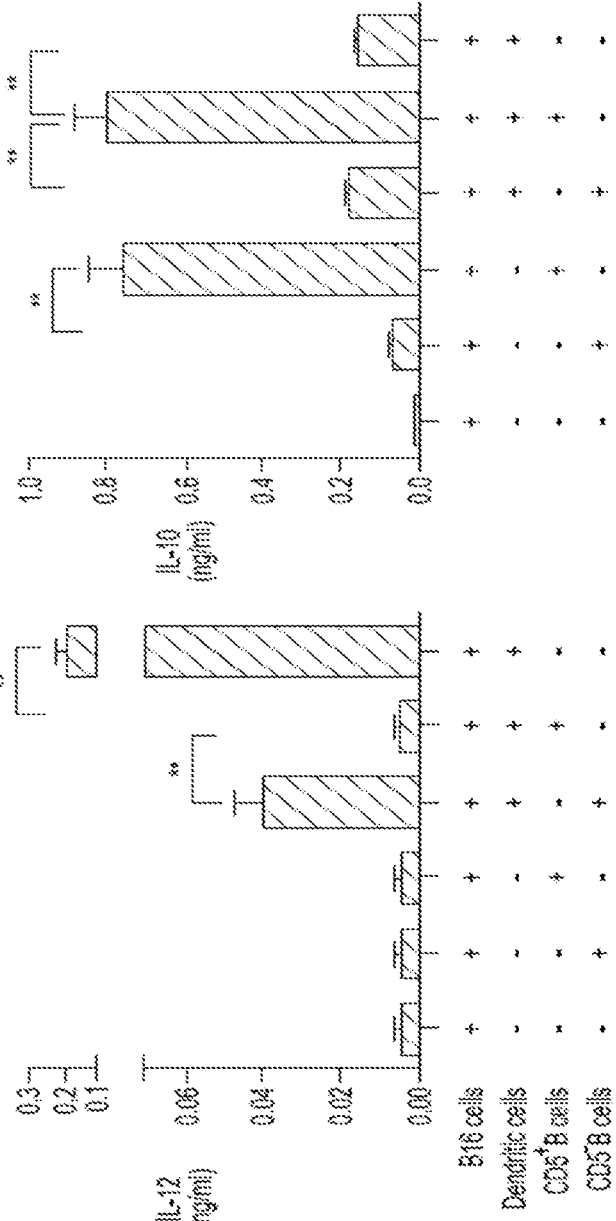
Figure 2A:
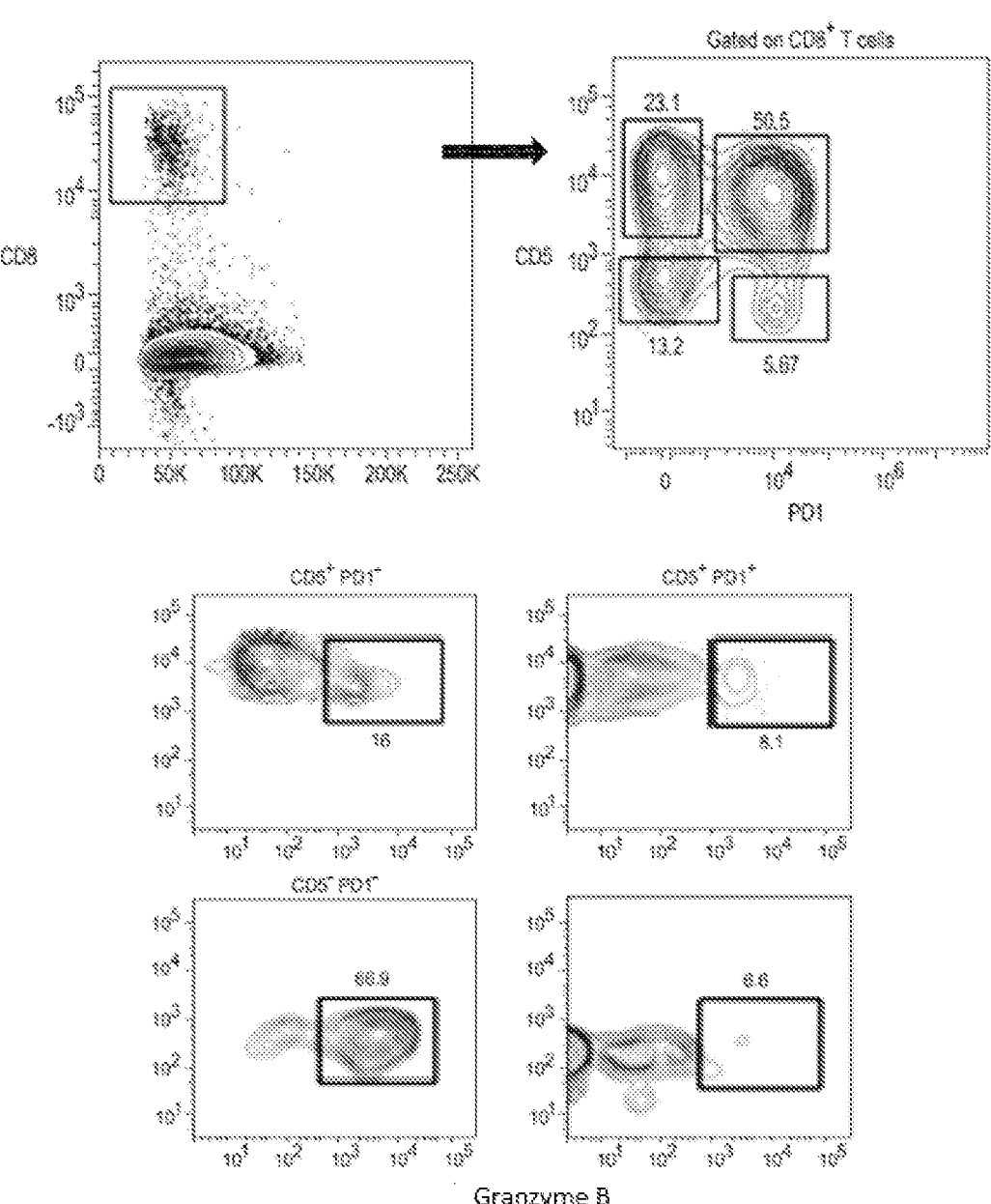
FIGS. 2A-2E present illustrative data showing that CD5 and PD1 expression mediated the tumor CD8$^+$ TEFF cell inhibition and CD5-blocking antibody enhanced IFNy expression and dramatically increased PDL1 blockade induced CD8$^+$ T cell effect function.
Figure 2B:
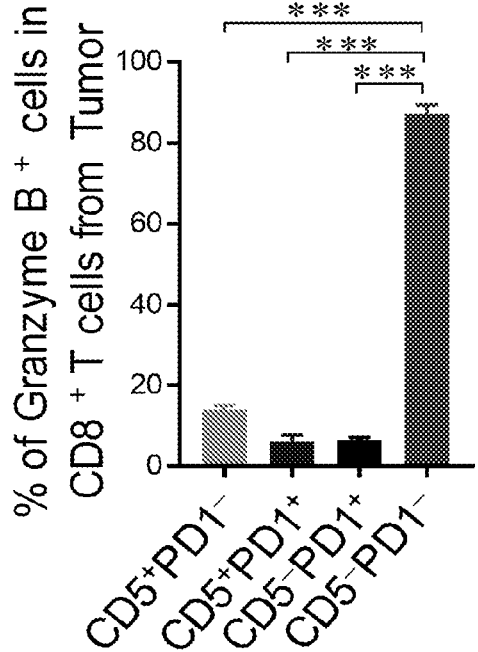
Figure 2C:
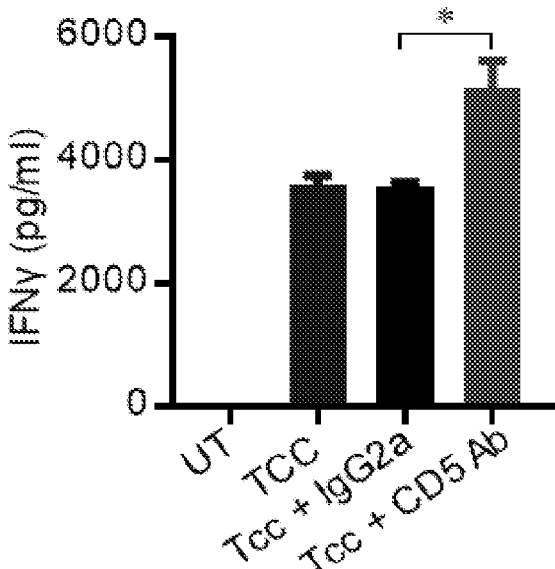
Figure 2D:
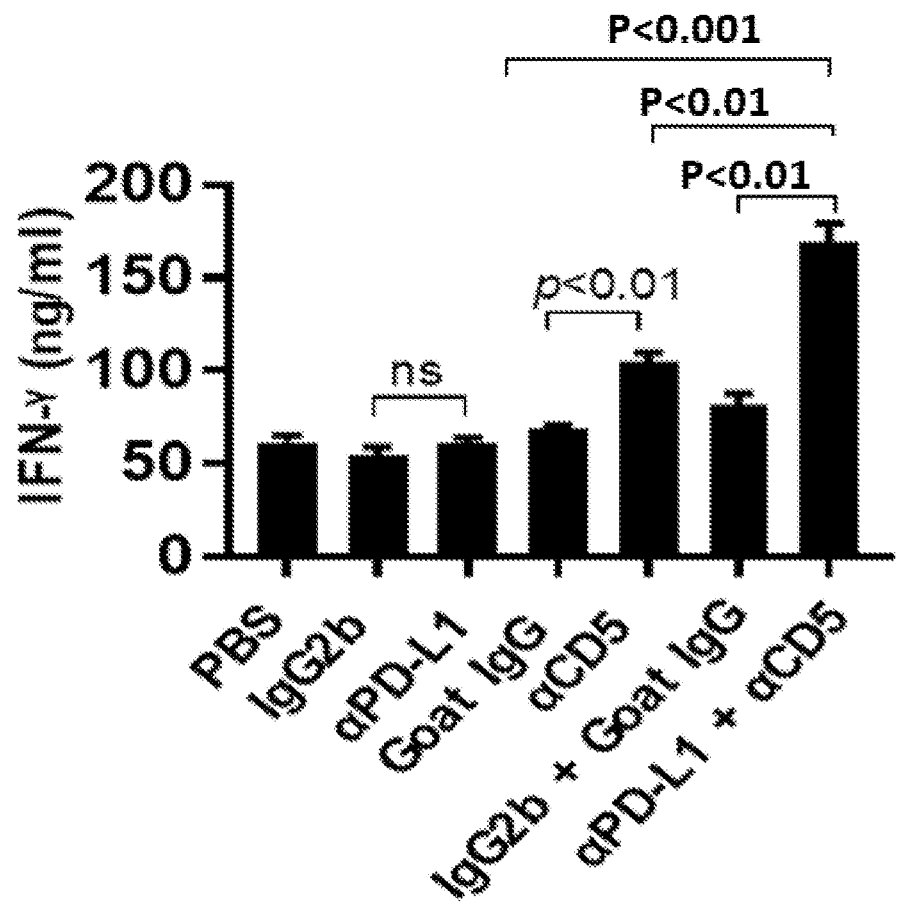
Figure 2E:
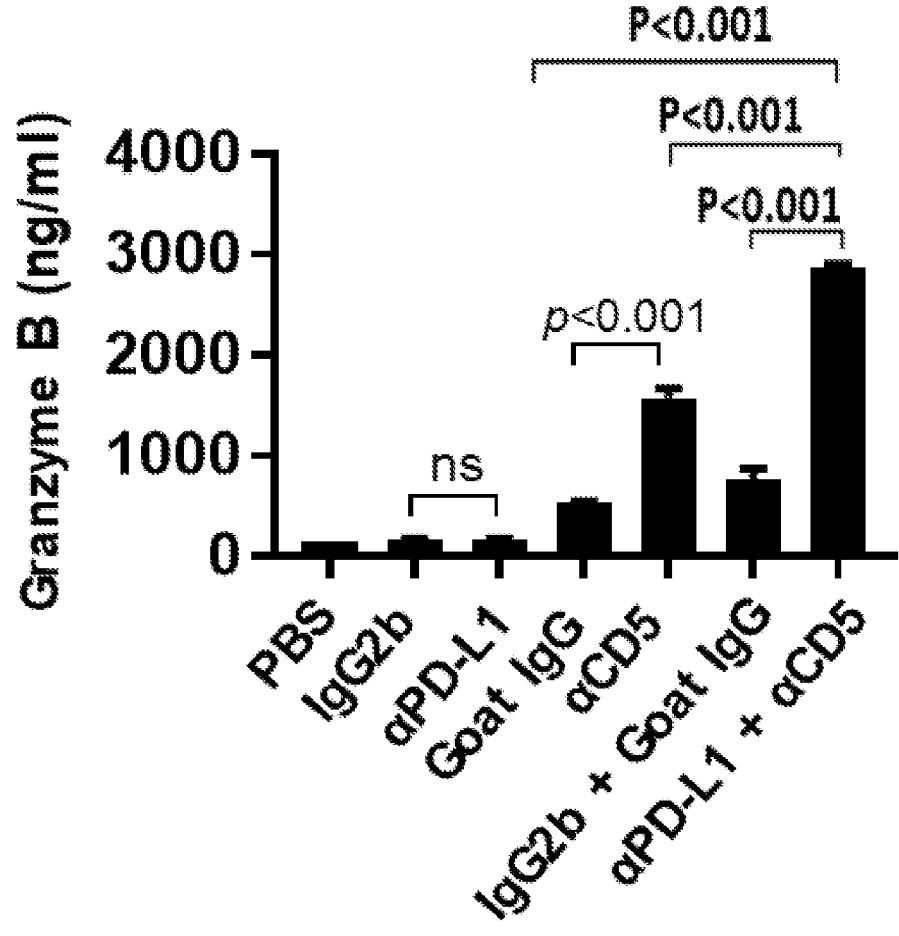

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nucl. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) or 10, M=5, N=−4 and a comparison of both strands. For amino acid sequences, the BLASTP program uses as defaults a word length of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

Antibodies are large, complex molecules (molecular weight of 150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region, involved in binding the target antigen, and a constant ("C") region that interacts with other components of the immune system. The light and heavy chain variable regions (also referred to herein as light chain variable (VL) domain and heavy chain variable (VH) domain, respectively) come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains (e.g., light chain variable domain, heavy chain variable domain) of an antibody or fragment thereof. Non-limiting examples of antibody variants include single-domain antibodies or nanobodies, mono-specific $Fab_2$, bispecific $Fab_2$, trispecific $Fab_3$, monovalent IgGs, scFv, bispecific antibodies, bispecific diabodies, trispecific triabodies, scFv-Fc, minibodies, IgNAR, V-NAR, hcIgG, VhH, or peptibodies. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805 which are incorporated by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The terms "CDR L1", "CDR L2" and "CDR L3" as provided herein refer to the complementarity determining regions (CDR) 1, 2, and 3 of the variable light (L) chain of an antibody. In embodiments, the variable light chain provided herein includes in N-terminal to C-terminal direction a CDR L1, a CDR L2 and a CDR L3. Likewise, the terms "CDR H1", "CDR H2" and "CDR H3" as provided herein refer to the complementarity determining regions (CDR) 1, 2, and 3 of the variable heavy (H) chain of an antibody. In embodiments, the variable heavy chain provided herein includes in N-terminal to C-terminal direction a CDR H1, a CDR H2 and a CDR H3.

The terms "FR L1", "FR L2", "FR L3" and "FR L4" as provided herein are used according to their common meaning in the art and refer to the framework regions (FR) 1, 2, 3 and 4 of the variable light (L) chain of an antibody. In embodiments, the variable light chain provided herein includes in N-terminal to C-terminal direction a FR L1, a FR L2, a FR L3 and a FR L4. Likewise, the terms "FR H1", "FR H2", "FR H3" and "FR H4" as provided herein are used according to their common meaning in the art and refer to the framework regions (FR) 1, 2, 3 and 4 of the variable heavy (H) chain of an antibody. In embodiments, the variable heavy chain provided herein includes in N-terminal to C-terminal direction a FR H1, a FR H2, a FR H3 and a FR H4.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL), variable light chain (VL) domain or light chain variable region and variable heavy chain (VH), variable heavy chain (VH) domain or heavy chain variable region refer to these light and heavy chain regions, respectively. The terms variable light chain (VL), variable light chain (VL) domain and light chain variable region as referred to herein may be used interchangeably. The terms variable heavy chain (VH), variable heavy chain (VH) domain and heavy chain variable region as referred to herein may be used interchangeably. The Fc (i.e. fragment crystallizable region) is the "base" or "tail" of an immunoglobulin and is typically composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)). The term "antibody" as referred to herein further includes antibody variants such as single domain antibodies. Thus, in embodiments an antibody includes a single monomeric variable antibody domain. Thus, in embodiments, the antibody, includes a variable light chain (VL) domain or a variable heavy chain (VH) domain. In embodiments, the antibody is a variable light chain (VL) domain or a variable heavy chain (VH) domain. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

For preparation of monoclonal or polyclonal antibodies, any technique known in the art can be used (see, e.g., Kohler & Milstein, *Nature* 256:495-497 (1975); Kozbor et al., *Immunology Today* 4:72 (1983); Cole et al., pp. 77-96 in *Monoclonal Antibodies and Cancer Therapy* (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552-554 (1990); Marks et al., *Biotechnology* 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633, 425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern.

Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "ligand" refers to an agent, e.g., a polypeptide or other molecule, capable of binding to a receptor or antibody, antibody variant, antibody region or fragment thereof.

The term "CD5" as used herein refers to any recombinant or naturally-occurring forms of cluster of differentiation 5 (CD5) or variants or homologs thereof that maintain CD5 activity (e.g. within at least 50%, 80%, 90%, 95%, 96%, 97%, 98%, 99% or 100% activity compared to CD5). In embodiments, the variants or homologs have at least 90%, 95%, 96%, 97%, 98%, 99% or 100% amino acid sequence identity across the whole sequence or a portion of the sequence (e.g. a 10, 20, 50, 100, 150 or 200 continuous amino acid portion) compared to a naturally occurring CD5 polypeptide. In embodiments, CD5 is substantially identical to the protein identified by the UniProt reference number 043866 or a variant or homolog having substantial identity thereto. In embodiments, CD5 is the protein identified by the UniProt reference number 043866 or a variant or homolog having substantial identity thereto.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

"Contacting" is used in accordance with its plain ordinary meaning and refers to the process of allowing at least two distinct species (e.g. antibodies and antigens) to become sufficiently proximal to react, interact, or physically touch. It should be appreciated; however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell. In embodiments contacting includes, for example, allowing a pharmaceutical composition as described herein to interact with a cell.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include, but are not limited to, yeast cells and cells derived from plants and animals, for example mammalian, insect (e.g., spodoptera) and human cells.

A "stem cell" as provided herein refers to a cell characterized by the ability of self-renewal through mitotic cell division and the potential to differentiate into a tissue or an organ. Among mammalian stem cells, embryonic stem cells (ES cells) and somatic stem cells (e.g., HSC) can be distinguished. Embryonic stem cells reside in the blastocyst and give rise to embryonic tissues, whereas somatic stem cells reside in adult tissues for the purpose of tissue regeneration and repair. In embodiments, the stem cell is a leukemia stem cell (LSC). A "leukemia stem cell or "LSC" as provided herein refers to a cell capable of initiating the disease (leukemia) when transplanted into immunodeficient animals and can self-renew by giving rise to leukemia in serial transplantations and also partially differentiate into non-LSC bulk blasts that resemble the original disease but are unable to self-renew. An LSC may carry a gene mutation and be able to self-renew through mitotic cell division and differentiate into the hematopoietic lineage carrying said gene mutant or an LSC may remain as immature progenitor cells, also known as blast cells. In embodiments, the LSC expresses CD34.

"B Cells" or "B lymphocytes" refer to their standard use in the art. B cells are lymphocytes, a type of white blood cell (leukocyte), that develops into a plasma cell (a "mature B cell"), which produces antibodies. An "immature B cell" is a cell that can develop into a mature B cell. Generally, pro-B cells undergo immunoglobulin heavy chain rearrangement to become pro B pre B cells, and further undergo immunoglobulin light chain rearrangement to become an immature B cells. Immature B cells include T1 and T2 B cells.

"T cells" or "T lymphocytes" as used herein are a type of lymphocyte (a subtype of white blood cell) that plays a central role in cell-mediated immunity. They can be distinguished from other lymphocytes, such as B cells and natural killer cells, by the presence of a T-cell receptor on the cell surface. T cells include, for example, natural killer T (NKT) cells, cytotoxic T lymphocytes (CTLs), regulatory T (Treg) cells, and T helper cells. Different types of T cells can be distinguished by use of T cell detection agents.

As defined herein, the term "inhibition", "inhibit", "inhibiting" and the like in reference to a protein-inhibitor (e.g., an A2A receptor antagonist or a PD-1 signaling pathway inhibitor) interaction means negatively affecting (e.g., decreasing) the activity or function of the protein (e.g., decreasing the activity of an A2A receptor or a PD-1 protein or PD-L1 protein) relative to the activity or function of the protein in the absence of the inhibitor (e.g., an A2A receptor antagonist or a PD-1 signaling pathway inhibitor). In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., an A2A receptor or a PD-1 protein or PD-L1 protein). Similarly an "inhibitor" is a compound or protein that inhibits an A2A receptor or a PD-1 protein or PD-L1 protein, e.g., by binding, partially or totally blocking, decreasing, preventing, delaying, inactivating, desensitizing, or down-regulating activity (e.g., an A2A receptor activity or a PD-1 protein activity or PD-L1 protein activity).

A "PD-1 protein" or "PD-1" as referred to herein includes any of the recombinant or naturally-occurring forms of the Programmed cell death protein 1 (PD-1) also known as cluster of differentiation 279 (CD 279) or variants or homologs thereof that maintain PD-1 protein activity (e.g. within at least 50%, 80%, 90%, 95%, 96%, 97%, 98%, 99% or 100% activity compared to PD-1 protein). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PD-1 protein. In embodiments, the PD-1 protein is substantially identical to the protein identified by the UniProt reference number Q15116 or a variant or homolog having substantial identity thereto. In embodiments, the PD-1 protein is substantially identical to the protein identified by the UniProt reference number Q02242 or a variant or homolog having substantial identity thereto. In embodiments, the PD-1 inhibitor is Nivolumab, Pembrolizumab, or Cemiplimab. In embodiments, the PD-1 inhibitor is Nivolumab. In embodiments, the PD-1 inhibitor is Pembrolizumab. In embodiments, the PD-1 inhibitor is Cemiplimab.

The term "cemiplimab" as provided herein refers to a monoclonal antibody capable of binding the programmed death receptor-1 (PD-1). In the usual and customary sense "cemiplimab" refers to the antibody identified by Cas Registry number 1801342-60-8.

The term "pembrolizumab" as provided herein refers to a humanized antibody capable of binding the programmed death receptor-1 (PD-1). In the usual and customary sense "pembrolizumab" refers to the antibody identified by Cas Registry number 1374853-91-4.

The term "nivolumab" as provided herein refers to a monoclonal antibody capable of binding the programmed death receptor-1 (PD-1). In the usual and customary sense "nivolumab" refers to the antibody identified by Cas Registry number 946414-94-4.

The term "CD34" as referred to herein includes any of the recombinant or naturally-occurring forms of the cluster of differentiation 34 protein, or variants or homologs thereof that maintain CD34 activity (e.g. within at least 50%, 80%, 90%, 95%, 96%, 97%, 98%, 99% or 100% activity compared to CD34). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD34 protein. In embodiments, the CD34 protein is substantially identical to the protein identified by the UniProt reference number P28906 or a variant or homolog having substantial identity thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "exogenous" refers to a molecule or substance (e.g., a compound, nucleic acid or protein) that originates from outside a given cell or organism. For example, an "exogenous promoter" as referred to herein is a promoter that does not originate from the cell or organism it is expressed by. Conversely, the term "endogenous" or "endogenous promoter" refers to a molecule or substance that is native to, or originates within, a given cell or organism.

As defined herein, the term "inhibition", "inhibit", "inhibiting" and the like in reference to cell proliferation (e.g., cancer cell proliferation) means negatively affecting (e.g., decreasing proliferation) or killing the cell. In some embodiments, inhibition refers to reduction of a disease or symptoms of disease (e.g., cancer, cancer cell proliferation). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound or protein that inhibits a receptor or another protein, e.g., by binding, partially or totally blocking, decreasing, preventing, delaying, inactivating, desensitizing, or down-regulating activity (e.g., a receptor activity or a protein activity).

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, synoviocytes, synovial fluid, synovial tissue, fibroblast-like synoviocytes, macrophage like synoviocytes, etc.).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with the compounds or methods provided herein. The disease may be a cancer. In some further instances, "cancer" refers to human cancers and carcinomas, sarcomas, adenocarcinomas, lymphomas, leukemias, including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including acute myeloid leukemia (AML), ALL, and CML), or multiple myeloma.

As used herein, the term "cancer" refers to all types of cancer, neoplasm or malignant tumors found in mammals (e.g., humans), including leukemia, carcinomas and sarcomas. Exemplary cancers that may be treated with a compound or method provided herein include breast cancer, colon cancer, kidney cancer, leukemia, lung cancer, melanoma, ovarian cancer, prostate cancer, pancreatic cancer, brain cancer, liver cancer, gastric cancer or a sarcoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute myeloid leukemia, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epidermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer (e.g. leukemia, acute myeloid leukemia)) means that the disease (e.g., cancer (e.g. leukemia, acute myeloid leukemia)) is caused by (in whole or in part), or a symptom of the disease is caused by (in whole or in part) the substance or substance activity or function. Alternatively, the substance (e.g., CD5) may be an indicator of the disease (e.g., cancer (e.g. leukemia, acute myeloid leukemia)). Thus, an associated substance may serve as a means of targeting disease tissue (e.g., cancer cells (e.g., leukemia stem cells, acute myeloid leukemia cells)).

As used herein, "treating" or "treatment of" a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it involves halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

The terms "dose" and "dosage" are used interchangeably herein. A dose refers to the amount of active ingredient given to an individual at each administration. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical or pharmaceutical composition, and depends on the route of administration. For example, a dosage form can be in a liquid form for nebulization, e.g., for inhalants, in a tablet or liquid, e.g., for oral delivery, or a saline solution, e.g., for injection.

By "therapeutically effective dose or amount" as used herein is meant a dose that produces effects for which it is administered (e.g. treating or preventing a disease). The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

A "synergistic amount" as used herein refers to the sum of a first amount (e.g., an amount of a compound provided herein) and a second amount (e.g., a therapeutic agent) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

Antibody Compositions

CD5 activates STAT3 in both tumor-associated B cells and T cells, leading to immune-suppression. Applicants show that the antibody compositions (e.g., antibodies, chimeric antigen receptors, bispecific antibodies) and methods provided herein effectively block CD5 in tumor-associated T cells and may have stronger immunostimulatory effects than the use of PD-1 antibodies. The antibody compositions provided herein are capable of eliciting human T cell activation and are superior compared to other previously known CD5 antibodies. Applicants further demonstate that when the antibody compositions provided herein, including embodiments thereof, are used in combination with anti-PD-1 antibodies, a synergy in human T cell activation may be detected.

Provided herein are, inter alia, antibodies (e.g., humanized antibodies, monoclonal antibodies) and antibody compositions (e.g., chimeric antigen receptors, bispecific antibodies) that are capable of binding CD5. The antibodies and antibody compositions provided herein include novel light and heavy chain domain CDRs and framework regions, and bind CD5 with high efficiency and specificity, thereby effectively targeting CD5 expressing cells. The light and heavy chain domains of the antibodies provided herein may form part of recombinant proteins also referred to herein as antibody compositions (e.g., chimeric antigen receptors or bispecific antibodies) to be used, inter alia, as cancer therapeutics and for diagnostic purposes.

In an aspect is provided an anti-cluster of differentiation 5 (CD5) antibody including a light chain variable domain and a heavy chain variable domain, wherein the light chain variable domain includes: a CDR L1 as set forth in SEQ ID NO:1, a CDR L2 as set forth in SEQ ID NO:2 and a CDR L3 as set forth in SEQ ID NO:3; and wherein the heavy chain variable domain includes: a CDR H1 as set forth in SEQ ID NO:4, a CDR H2 as set forth in SEQ ID NO:5, and a CDR H3 as set forth in SEQ ID NO:6.

As described above, a "light chain variable (VL) domain" as provided herein refers to the variable region of the light chain of an antibody, an antibody variant or fragment thereof. Likewise, the "heavy chain variable (VH) domain" as provided herein refers to the variable region of the heavy chain of an antibody, an antibody variant or fragment thereof. The light chain variable domain and the heavy chain variable domain together form the paratope, which binds an antigen (epitope). The paratope or antigen-binding site is formed at the N-terminus of an antibody, an antibody variant or fragment thereof. In embodiments, the light chain variable (VL) domain includes CDR L1, CDR L2, CDR L3 and FR L1, FR L2, FR L3 and FR L4 (framework regions) of an antibody light chain. In embodiments, the heavy chain variable (VH) domain includes CDR H1, CDR H2, CDR H3 and FR H1, FR H2, FR H3 and FR H4 (framework regions) of an antibody heavy chain. In embodiments, the light chain variable (VL) domain and a light chain constant (CL) domain form part of an antibody light chain. In embodiments, the heavy chain variable (VH) domain and a heavy chain constant (CH1) domain form part of an antibody heavy chain. In embodiments, the heavy chain variable (VH) domain and one or more heavy chain constant (CH1, CH2, or CH3) domains form part of an antibody heavy chain. Thus, in embodiments, the light chain variable (VL) domain forms part of an antibody. In embodiments, the heavy chain variable (VH) domain forms part of an antibody. In embodiments, the light chain variable (VL) domain forms part of a therapeutic antibody. In embodiments, the heavy chain variable (VH) domain forms part of a therapeutic antibody. In embodiments, the light chain variable (VL) domain forms part of a human antibody. In embodiments, the heavy chain variable (VH) domain forms part of a human antibody. In embodiments, the light chain variable (VL) domain forms part of a humanized antibody. In embodiments, the heavy chain variable (VH) domain forms part of a humanized antibody. In embodiments, the light chain variable (VL) domain forms part of a chimeric antibody. In embodiments, the heavy chain variable (VH) domain forms part of a chimeric antibody. In embodiments, the light chain variable (VL) domain forms part of an antibody fragment. In embodiments, the heavy chain variable (VH) domain forms part of an antibody fragment. In embodiments, the light chain variable (VL) domain forms part of an antibody variant. In embodiments, the heavy chain variable (VH) domain forms part of an antibody variant. In embodiments, the light chain variable (VL) domain forms part of a Fab. In embodiments, the heavy chain variable (VH) domain forms part of a Fab. In embodiments, the light chain variable (VL) domain forms part of a scFv. In embodiments, the heavy chain variable (VH) domain forms part of a scFv.

In embodiments, the light chain variable domain includes a FR L1 as set forth in SEQ ID NO:7, a FR L2 as set forth in SEQ ID NO:8, a FR L3 as set forth in SEQ ID NO:9 and a FR L4 as set forth in SEQ ID NO:10. In embodiments, the heavy chain variable domain includes a FR H1 as set forth in SEQ ID NO:11, a FR H2 as set forth in SEQ ID NO:12, a FR H3 as set forth in SEQ ID NO:13 and a FR H4 as set forth in SEQ ID NO:14.

In embodiments, the light chain variable domain includes: a CDR L1 as set forth in SEQ ID NO:1, a CDR L2 as set forth in SEQ ID NO:2, a CDR L3 as set forth in SEQ ID NO:3, a FR L1 as set forth in SEQ ID NO:7, a FR L2 as set forth in SEQ ID NO:8, a FR L3 as set forth in SEQ ID NO:9 and a FR L4 as set forth in SEQ ID NO:10 and the heavy chain variable domain includes: a CDR H1 as set forth in SEQ ID NO:4, a CDR H2 as set forth in SEQ ID NO:5, and a CDR H3 as set forth in SEQ ID NO:6. In embodiments, the light chain variable domain includes: a CDR L1 as set forth in SEQ ID NO:1, a CDR L2 as set forth in SEQ ID NO:2 and a CDR L3 as set forth in SEQ ID NO:3; and the heavy chain variable domain includes: a CDR H1 as set forth in SEQ ID NO:4, a CDR H2 as set forth in SEQ ID NO:5, a CDR H3 as set forth in SEQ ID NO:6, a FR H1 as set forth in SEQ ID NO:11, a FR H2 as set forth in SEQ ID NO:12, a FR H3 as set forth in SEQ ID NO:13 and a FR H4 as set forth in SEQ ID NO:14.

In one embodiment, the light chain variable domain includes: a CDR L1 as set forth in SEQ ID NO:1, a CDR L2 as set forth in SEQ ID NO:2, a CDR L3 as set forth in SEQ ID NO:3, a FR L1 as set forth in SEQ ID NO:7, a FR L2 as set forth in SEQ ID NO:8, a FR L3 as set forth in SEQ ID NO:9 and a FR L4 as set forth in SEQ ID NO:10 and the heavy chain variable domain includes: a CDR H1 as set forth in SEQ ID NO:4, a CDR H2 as set forth in SEQ ID NO:5, a CDR H3 as set forth in SEQ ID NO:6, a FR H1 as set forth in SEQ ID NO:11, a FR H2 as set forth in SEQ ID NO:12, a FR H3 as set forth in SEQ ID NO:13 and a FR H4 as set forth in SEQ ID NO:14. In one further embodiment, the antibody is antibody 9F2A11.

In embodiments, the light chain variable domain includes the sequence of SEQ ID NO:15. In embodiments, the light chain variable domain is the sequence of SEQ ID NO:15. In embodiments, the heavy chain variable domain includes the sequence of SEQ ID NO:16. In embodiments, the heavy chain variable domain is the sequence of SEQ ID NO:16. In embodiments, the light chain variable domain includes the sequence of SEQ ID NO:15 and the heavy chain variable domain includes the sequence of SEQ ID NO:16. In embodiments, the light chain variable domain is the sequence of SEQ ID NO:15 and the heavy chain variable domain is the sequence of SEQ ID NO:16.

In embodiments, the antibody is a humanized antibody. In embodiments, the antibody is a chimeric antibody. In embodiments, the antibody is a Fab' fragment. In embodiments, the antibody is a single chain antibody (scFv). In embodiments, the light chain variable domain and the heavy chain variable domain form part of a scFv. In embodiments, the scFv includes the sequence of SEQ ID NO:15. In embodiments, the scFv includes the sequence of SEQ ID NO:15 and the sequence of SEQ ID NO:16.

In embodiments, the antibody is an IgG. In embodiments, the antibody is an IgG1. In embodiments, the antibody is a human IgG.

In embodiments, the antibody is capable of binding CD5. In embodiments, the antibody is bound to CD5. In embodiments, the CD5 forms part of a cell. In embodiments, the cell is a lymphoid cell. In embodiments, the cell is a B cell or a T cell. In embodiments, the cell is a B cell. In embodiments, the cell is a T cell. In embodiments, the antibody is attached to a detectable label.

Recombinant Protein Compositions

As described above, the light chain variable (VL) domain and the heavy chain variable (VH) domain provided herein including embodiments thereof, may each independently form part of an antibody, an antibody variant, a fragment of an antibody, a fragment of an antibody variant, or a recombinant protein (e.g., a chimeric antigen receptor, bispecific antibody). Provided herein are, inter alia, recombinant proteins (e.g., a chimeric antigen receptor, a bispecific antibody), which include the light chain variable (VL) domain and/or the heavy chain variable (VH) domain as provided herein and are therefore capable of binding CD5 and recruiting effector cells to CD5-expressing cells (e.g., T cells), thereby effectively inhibiting CD5 activity and mediating the reversal of immune-suppression caused by CD5 activity. In embodiments, the recombinant protein is a chimeric antigen receptor (CAR). In embodiments, the recombinant protein is a bispecific antibody.

Chimeric Antigen Receptor Proteins

Provided herein are, inter alia, recombinant proteins, wherein the recombinant protein is a chimeric antigen receptor. The antibody region of the recombinant protein may include any of the light chain and heavy chain variable domains provided herein including embodiments thereof. The light chain variable (VL) domain and/or the heavy chain variable (VH) domain as provided herein may form part of a chimeric antigen receptor. Thus, in an aspect is provided a recombinant protein including: (i) an antibody region including: (a) a heavy chain variable domain including a CDR H1 as set forth in SEQ ID NO:1, a CDR H2 as set forth in SEQ ID NO:2 and a CDR H3 as set forth in SEQ ID NO:3; and (b) a light chain variable domain including a CDR L1 as set forth in SEQ ID NO:4, a CDR L2 as set forth in SEQ ID NO:5, and a CDR L3 as set forth in SEQ ID NO:6; and (ii) a transmembrane domain.

An "antibody region" as provided herein refers to a monovalent or multivalent protein moiety that forms part of the recombinant protein (e.g., CAR) provided herein including embodiments thereof. A person of ordinary skill in the art will therefore immediately recognize that the antibody region is a protein moiety capable of binding an antigen (epitope). Thus, the antibody region provided herein may include a domain of an antibody (e.g., a light chain variable (VL) domain, a heavy chain variable (VH) domain) or a fragment of an antibody (e.g., Fab). In embodiments, the antibody region is a protein conjugate. A "protein conjugate" as provided herein refers to a construct consisting of more than one polypeptide, wherein the polypeptides are bound together covalently or non-covalently. In embodiments, the protein conjugate includes a Fab moiety (a monovalent Fab) covalently attached to an scFv moiety (a monovalent scFv). In embodiments, the protein conjugate includes a plurality (at least two) Fab moieties. In embodiments, the polypeptides of a protein conjugate are encoded by one nucleic acid molecule. In embodiments, the polypeptides of a protein conjugate are encoded by different nucleic acid molecules. In embodiments, the polypeptides are connected through a linker. In embodiments, the polypeptides are connected through a chemical linker. In embodiments, the antibody region is an scFv. The antibody region may include a light chain variable (VL) domain and/or a heavy chain variable (VH) domain.

A "transmembrane domain" as provided herein refers to a polypeptide forming part of a biological membrane. The transmembrane domain provided herein is capable of spanning a biological membrane (e.g., a cellular membrane) from one side of the membrane through to the other side of the membrane. In embodiments, the transmembrane domain spans from the intracellular side to the extracellular side of a cellular membrane. Transmembrane domains may include non-polar, hydrophobic residues, which anchor the proteins provided herein including embodiments thereof in a biological membrane (e.g., cellular membrane of a T cell). Any transmembrane domain capable of anchoring the proteins provided herein including embodiments thereof are contemplated. Non-limiting examples of transmembrane domains include the transmembrane domains of CD28, CD8, CD4 or CD3-zeta. In embodiments, the transmembrane domain is a CD4 transmembrane domain.

In embodiments, the transmembrane domain is a CD28 transmembrane domain. The term "CD28 transmembrane domain" as provided herein includes any of the recombinant or naturally-occurring forms of the transmembrane domain of CD28, or variants or homologs thereof that maintain CD28 transmembrane domain activity (e.g. within at least 50%, 80%, 90%, 95%, 96%, 97%, 98%, 99% or 100% activity compared to the CD28 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 transmembrane domain polypeptide. In embodiments, CD28 is the protein as identified by the NCBI sequence reference GI:340545506, homolog or functional fragment thereof.

In embodiments, the transmembrane domain is a CD8 transmembrane domain. The term "CD8 transmembrane domain" as provided herein includes any of the recombinant or naturally-occurring forms of the transmembrane domain of CD8, or variants or homologs thereof that maintain CD8 transmembrane domain activity (e.g. within at least 50%, 80%, 90%, 95%, 96%, 97%, 98%, 99% or 100% activity compared to the CD8 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD8 transmembrane domain polypeptide. In embodiments, CD8 is the protein as identified by the NCBI sequence reference GI:225007534, homolog or functional fragment thereof.

In embodiments, the transmembrane domain is a CD4 transmembrane domain. The term "CD4 transmembrane domain" as provided herein includes any of the recombinant or naturally-occurring forms of the transmembrane domain of CD4, or variants or homologs thereof that maintain CD4 transmembrane domain activity (e.g. within at least 50%, 80%, 90%, 95%, 96%, 97%, 98%, 99% or 100% activity compared to the CD4 transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD4 transmembrane domain polypeptide. In embodiments, CD4 is the protein as identified by the NCBI sequence reference GI:303522473, homolog or functional fragment thereof.

In embodiments, the transmembrane domain is a CD3-zeta (also known as CD247) transmembrane domain. The term "CD3-zeta transmembrane domain" as provided herein includes any of the recombinant or naturally-occurring forms of the transmembrane domain of CD3-zeta, or variants or homologs thereof that maintain CD3-zeta transmembrane domain activity (e.g. within at least 50%, 80%, 90%, 95%, 96%, 97%, 98%, 99% or 100% activity compared to the CD3-zeta transmembrane domain). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3-zeta transmembrane domain polypeptide. In embodiments, CD3-zeta is the protein as identified by the NCBI sequence reference GI:166362721, homolog or functional fragment thereof.

The recombinant proteins (e.g., chimeric antigen receptors) provided herein may include any of the CD5 antibodies or fragments thereof described herein. Thus, the recombinant proteins (e.g., chimeric antigen receptors) may include any of the CDRs, FRs, heavy chain variable domains, or light chain variable domains provided herein. For example, the heavy chain variable domain may include the sequence of SEQ ID NO:16. In embodiments, the heavy chain variable domain is the sequence of SEQ ID NO:16. For example, the light chain variable domain may include the sequence of SEQ ID NO:15. In embodiments, light chain variable domain is the sequence of SEQ ID NO:15.

In embodiments, the recombinant protein is bound to a CD5 protein. In embodiments, the CD5 protein is a human CD5 protein. In embodiments, the CD5 protein forms part of a cell. In embodiments, the CD5 protein is expressed on the surface of the cell.

In embodiments, the antibody region includes an Fc domain. In embodiments, the antibody region includes a spacer region. In embodiments, the spacer region is between the transmembrane domain and the antibody region. A "spacer region" as provided herein is a polypeptide connecting the antibody region with the transmembrane domain. In embodiments, the spacer region connects the heavy chain constant region with the transmembrane domain. In embodiments, the spacer region includes an Fc region. In embodiments, the spacer region is an Fc region. Examples of spacer regions contemplated for the recombinant protein compositions provided herein include without limitation, immunoglobulin molecules or fragments thereof (e.g., IgG1, IgG2, IgG3, IgG4) and immunoglobulin molecules or fragments thereof (e.g., IgG1, IgG2, IgG3, IgG4) including mutations affecting Fc receptor binding. In embodiments, the spacer region is a hinge region.

In embodiments, the recombinant protein as provided herein, including embodiments thereof, further includes an intracellular co-stimulatory signaling domain. An "intracellular co-stimulatory signaling domain" as provided herein includes amino acid sequences capable of providing co-stimulatory signaling in response to binding of an antigen to the antibody region provided herein including embodiments thereof. In embodiments, the signaling of the co-stimulatory signaling domain results in production of cytokines and proliferation of the T cell expressing the same. In embodiments, the intracellular co-stimulatory signaling domain is a CD28 intracellular co-stimulatory signaling domain, a 4-1BB intracellular co-stimulatory signaling domain, a ICOS intracellular co-stimulatory signaling domain, or an OX-40 intracellular co-stimulatory signaling domain. In embodiments, the intracellular co-stimulatory signaling domain is a CD28 intracellular co-stimulatory signaling domain. In embodiments, the intracellular co-stimulatory signaling domain is a 4-1BB intracellular co-stimulatory signaling domain. In embodiments, the intracellular co-stimulatory signaling domain is a ICOS intracellular co-stimulatory signaling domain. In embodiments, the intracellular co-stimulatory signaling domain is an OX-40 intracellular co-stimulatory signaling domain.

In embodiments, the recombinant protein as provided herein including embodiments thereof, further includes an intracellular T-cell signaling domain. An "intracellular T-cell signaling domain" as provided herein includes amino acid sequences capable of providing primary signaling in response to binding of an antigen to the antibody region provided herein including embodiments thereof. In embodiments, the signaling of the intracellular T-cell signaling domain results in activation of the T cell expressing the same. In embodiments, the signaling of the intracellular T-cell signaling domain results in proliferation (cell division) of the T cell expressing the same. In embodiments, the signaling of the intracellular T-cell signaling domain results expression by the T cell of proteins known in the art to characteristic of activated T cell (e.g., CTLA-4, PD-1, CD28, CD69). In embodiments, the intracellular T-cell signaling domain includes the signaling domain of the zeta chain of the human CD3 complex. In embodiments, the intracellular T-cell signaling domain is a CD3 intracellular T-cell signaling domain.

The term "CTLA-4" as referred to herein includes any of the recombinant or naturally-occurring forms of the cytotoxic T-lymphocyte-associated protein 4 protein, also known as CD152 (cluster of differentiation 152), or variants or homologs thereof that maintain CTLA-4 activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 protein. In embodiments, the CTLA-4 protein is substantially identical to the protein identified by the UniProt reference number P16410 or a variant or homolog having substantial identity thereto.

The term "CD28" as referred to herein includes any of the recombinant or naturally-occurring forms of the Cluster of Differentiation 28 protein, or variants or homologs thereof that maintain CD28 activity (e.g. within at least 50%, 80%, 90%, 95%, 96%, 97%, 98%, 99% or 100% activity compared to CD28). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD28 protein. In embodiments, the CD28 protein is substantially identical to the protein identified by the UniProt reference number P10747 or a variant or homolog having substantial identity thereto.

The term "CD69" as referred to herein includes any of the recombinant or naturally-occurring forms of the Cluster of Differentiation 69 protein, or variants or homologs thereof that maintain CD69 activity (e.g. within at least 50%, 80%, 90%, 95%, 96%, 97%, 98%, 99% or 100% activity compared to CD69). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD69 protein. In embodiments, the CD69 protein is substantially identical to the protein identified by the UniProt reference number Q07108 or a variant or homolog having substantial identity thereto.

The term "4-1BB" as referred to herein includes any of the recombinant or naturally-occurring forms of the 4-1BB protein, also known as tumor necrosis factor receptor superfamily member 9 (TNFRSF9), Cluster of Differentiation 137 (CD137) and induced by lymphocyte activation (ILA), or variants or homologs thereof that maintain 4-1BB activity (e.g. within at least 50%, 80%, 90%, 95%, 96%, 97%, 98%, 99% or 100% activity compared to 4-1BB). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the 4-1BB protein is substantially identical to the protein identified by the UniProt reference number Q07011 or a variant or homolog having substantial identity thereto.

In embodiments, the recombinant protein as provided herein including embodiments thereof, further includes a self-cleaving peptidyl sequence. In embodiments, the self-cleaving peptidyl linker sequence is a T2A sequence or a 2A sequence. In embodiments, the self-cleaving peptidyl linker sequence is a T2A sequence. In embodiments, the self-cleaving peptidyl linker sequence is a 2A sequence.

Bispecific Antibodies

The light chain variable (VL) domain and the heavy chain variable (VH) domain as provided herein may form part of a bispecific antibody. Thus, the second antibody region may include any of the light chain and/or heavy chain variable domains provided herein including embodiments thereof. In another aspect is provided a recombinant protein including: (i) a first antibody region capable of binding an effector cell ligand; and (ii) a second antibody region, including: (a) a light chain variable domain including a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6.

The term "effector cell ligand" as provided herein refers to a cell surface molecule expressed on an effector cell of the immune system (e.g., a cytotoxic T cell, a helper T cell, a B cell, a natural killer cell). Upon binding of the first antibody region to the effector cell ligand expressed on the effector cell, the effector cell is activated and able to exert its function (e.g., selective killing or eradication of malignant, infected or otherwise unhealthy cells). In embodiments, the effector cell ligand is a CD3 protein. In embodiments, the effector cell ligand is a CD16 protein. In embodiments, the effector cell ligand is a CD32 protein. In embodiments, the effector cell ligand is a NKp46 protein. The first antibody region as provided herein may be an antibody, an antibody variant, a fragment of an antibody or a fragment of an antibody variant.

A "CD3 protein" as referred to herein includes any of the recombinant or naturally-occurring forms of the Cluster of Differentiation 3 (CD3) proteins or variants or homologs thereof that comprise the CD3 complex that mediates signal transduction and maintains CD3 complex activity (e.g. within at least 50%, 80%, 90%, 95%, 96%, 97%, 98%, 99% or 100% activity compared to the CD3 complex). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD3 proteins in the CD3 complex.

A "CD16 protein" as referred to herein includes any of the recombinant or naturally-occurring forms of the Cluster of Differentiation 16 (CD16) protein, also known as low affinity immunoglobulin gamma Fc region receptor III-A, or variants or homologs thereof that maintain CD16 activity (e.g. within at least 50%, 80%, 90%, 95%, 96%, 97%, 98%, 99% or 100% activity compared to CD16). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD16 protein. In embodiments, the CD16 protein is substantially identical to the protein identified by the UniProt reference number P08637 or a variant or homolog having substantial identity thereto.

A "CD32 protein" as referred to herein includes any of the recombinant or naturally-occurring forms of the Cluster of Differentiation 32 (CD32) protein, also known as low affinity immunoglobulin gamma Fc region receptor II-A, or variants or homologs thereof that maintain CD32 activity (e.g. within at least 50%, 80%, 90%, 95%, 96%, 97%, 98%, 99% or 100% activity compared to CD32). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CD32 protein. In embodiments, the CD32 protein is substantially identical to the protein identified by the UniProt reference number P12318 or a variant or homolog having substantial identity thereto.

A "NKp46 protein" as referred to herein includes any of the recombinant or naturally-occurring forms of the NKp46 protein, also known as natural cytotoxicity triggering receptor 1, or variants or homologs thereof that maintain NKp46 activity (e.g. within at least 50%, 80%, 90%, 95%, 96%, 97%, 98%, 99% or 100% activity compared to NKp46). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NKp46 protein. In embodiments, the NKp46 protein is substantially identical to the protein identified by the UniProt reference number 076036 or a variant or homolog having substantial identity thereto.

The recombinant proteins (e.g., bispecific antibody) provided herein may include any of the CD5 antibodies or fragments thereof described herein. Thus, the recombinant protein (e.g., bispecific antibody) may include any of the CDRs, FRs, heavy chain variable domains, or light chain variable domains provided herein. For example, the heavy chain variable domain may include the sequence of SEQ ID NO:16. In embodiments, the heavy chain variable domain is the sequence of SEQ ID NO:16. For example, the light chain variable domain may include the sequence of SEQ ID NO:15. In embodiments, light chain variable domain is the sequence of SEQ ID NO:15.

The heavy chain variable domain of the recombinant protein (e.g., bispecific antibody) provided herein may include any of the CDRs or FRs provided herein. Thus, the heavy chain variable domain may include, for example, a FR H1 as set forth in SEQ ID NO:11, a FR H2 as set forth in SEQ ID NO:12, a FR H3 as set forth in SEQ ID NO:13, and a FR H4 as set forth in SEQ ID NO:14.

The light chain variable domain of the recombinant protein (e.g., bispecific antibody) provided herein may include any of the CDRs or FRs provided herein. For example, the light chain variable domain may include, for example, a FR L1 as set forth in SEQ ID NO:7, a FR L2 as set forth in SEQ ID NO:8, a FR L3 as set forth in SEQ ID NO:9, and a FR L4 as set forth in SEQ ID NO:10.

In embodiments, the first antibody region is a first Fab' fragment or the second antibody region is a second Fab' fragment. In embodiments, the first antibody region is a single chain variable fragment (scFv) or the second antibody region is a second single chain variable fragment (scFv).

In embodiments, the second antibody region is bound to an CD5. In embodiments, the CD5 is a human CD5. In embodiments, the CD5 forms part of a cell. In embodiments, the CD5 is expressed on the surface of the cell.

Nucleic Acid Compositions

The compositions provided herein include nucleic acid molecules encoding the anti-CD5 antibodies and recombinant proteins provided herein including embodiments thereof. Thus, in an aspect, an isolated nucleic acid encoding an antibody as provided herein including embodiments thereof is provided.

In another aspect, an isolated nucleic acid encoding a recombinant protein as provided herein, including embodiments thereof, is provided.

Pharmaceutical Compositions

The compositions provided herein include pharmaceutical compositions including therapeutically effective amount of the anti CD5 antibodies and recombinant proteins provided herein including embodiments thereof. Thus, in an aspect is provided a pharmaceutical composition including a therapeutically effective amount of an antibody as provided herein including embodiments thereof and a pharmaceutically acceptable excipient.

In another aspect is provided a pharmaceutical composition including a therapeutically effective amount of a recombinant protein as provided herein, including embodiments thereof, and a pharmaceutically acceptable excipient.

In embodiments, the pharmaceutical composition further includes a therapeutically effective amount of a Programmed Death 1 (PD-1) inhibitor. In embodiments, the PD-1 inhibitor is Nivolumab, Pembrolizumab, or Cemiplimab. In embodiments, the PD-1 inhibitor is Nivolumab. In embodiments, the PD-1 inhibitor is Pembrolizumab. In embodiments, the PD-1 inhibitor is Cemiplimab. In embodiments, the therapeutically effective amount of the antibody and the therapeutically effective amount of the PD-1 inhibitor is a combined synergistic amount.

Methods of Treatment

The compositions (e.g., the anti-CD5 antibodies and recombinant proteins) provided herein, including embodiments thereof, are contemplated as providing effective treatments for diseases such as cancer. Thus, in an aspect is provided a method of treating cancer in a subject in need thereof, the method including administering to a subject a therapeutically effective amount of an antibody as provided herein including embodiments thereof, thereby treating cancer in the subject.

In another aspect is provided a method of treating cancer in a subject in need thereof, the method including administering to a subject a therapeutically effective amount of a recombinant protein as described herein, including embodiments thereof, thereby treating cancer in the subject.

In embodiments, the cancer is lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, or neuroblastoma. In embodiments, the cancer is melanoma. In embodiments, the cancer is breast cancer. In embodiments, the cancer is pancreatic cancer.

In embodiments, the method further includes administering to the subject a second therapeutic agent. In embodiments, the method further includes administering a therapeutically effective amount of a PD-1 inhibitor. In embodiments, the effective amount of an antibody and the effective amount of a PD-1 inhibitor are a combined synergistic amount.

In embodiments, the antibody and the PD-1 inhibitor are administered sequentially or concurrently. In embodiments, the antibody and the PD-1 inhibitor are administered sequentially. In embodiments, the antibody and the PD-1 inhibitor are administered concurrently. In embodiments, the antibody and the PD-1 inhibitor are admixed together prior to administration. In embodiments, the antibody and the PD-1 inhibitor are administered in a single dosage form. In embodiments, the antibody and the PD-1 inhibitor are administered in two separate dosage forms.

In an aspect is provided a method of treating cancer in a subject in need thereof, the method including administering to a subject a combined effective amount of an antibody as provided herein including embodiments thereof and a PD-1 inhibitor, thereby treating cancer in the subject. In embodiments, the combined effective amount is a combined synergistic amount.

In embodiments, the effective amount of an antibody provided herein including embodiments thereof, and the effective amount of a PD-1 inhibitor are a combined synergistic amount. A "combined synergistic amount" as used herein refers to the sum of a first amount (e.g., an amount of an antibody provided herein including embodiments thereof) and a second amount (e.g., an amount of a PD-1 inhibitor), that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent. In embodiments, the measured effect of the compounds (e.g., the antibody provided herein and the PD-1 inhibitor) administered is 1-fold, 1.5-fold, 2-fold, 3-fold, 4-fold, 5-fold, 10-fold or greater than the sum of the individual effects of each of the compounds administered alone as a single agent.

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the PD-1 inhibitor when used separately from the antibody provided herein.

In embodiments, the antibody is administered at an amount from about 0.01 nM to about 10 nM. In embodiments, the antibody is administered at an amount from about 0.05 nM to about 10 nM. In embodiments, the antibody is administered at an amount from about 0.1 nM to about 10 nM. In embodiments, the antibody is administered at an amount from about 0.5 nM to about 10 nM. In embodiments, the antibody is administered at an amount from about 1 nM to about 10 nM. In embodiments, the antibody is administered at an amount from about 2 nM to about 10 nM. In embodiments, the antibody is administered at an amount from about 4 nM to about 10 nM. In embodiments, the antibody is administered at an amount from about 6 nM to about 10 nM. In embodiments, the antibody is administered at an amount from about 4 nM to about 10 nM. In embodiments, the antibody is administered at an amount from about 8 nM to about 10 nM. In embodiments, the antibody is administered at an amount of about 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from 0.01 nM to 10 nM. In embodiments, the antibody is administered at an amount from 0.05 nM to 10 nM. In embodiments, the antibody is administered at an amount from 0.1 nM to 10 nM. In embodiments, the antibody is administered at an amount from 0.5 nM to 10 nM. In embodiments, the antibody is administered at an amount from 1 nM to 10 nM. In embodiments, the antibody is administered at an amount from 2 nM to 10 nM. In embodiments, the antibody is administered at an amount from 4 nM to 10 nM. In embodiments, the antibody is administered at an amount from 6 nM to 10 nM. In embodiments, the antibody is administered at an amount from 4 nM to 10 nM. In embodiments, the antibody is administered at an amount from 8 nM to 10 nM. In embodiments, the antibody is administered at an amount of 0.01 nM, 0.05 nM, 0.1 nM, 0.5 nM, 1 nM, 2 nM, 2 nM, 4 nM, 5 nM, 6 nM, 7 nM, 8 nM, 9 nM or 10 nM.

In embodiments, the antibody is administered at an amount from about 0.01 nM to about 8 nM. In embodiments, the antibody is administered at an amount from about 0.05 nM to about 8 nM. In embodiments, the antibody is administered at an amount from about 0.1 nM to about 8 nM. In embodiments, the antibody is administered at an amount from about 0.5 nM to about 8 nM. In embodiments, the antibody is administered at an amount from about 1 nM to about 8 nM. In embodiments, the antibody is administered at an amount from about 2 nM to about 8 nM. In embodiments, the antibody is administered at an amount from about 4 nM to about 8 nM. In embodiments, the antibody is administered at an amount from about 6 nM to about 8 nM. In embodiments, the antibody is administered at an amount from about 4 nM to about 8 nM.

In embodiments, the antibody is administered at an amount from 0.01 nM to 8 nM. In embodiments, the antibody is administered at an amount from 0.05 nM to 8 nM. In embodiments, the antibody is administered at an amount from 0.1 nM to 8 nM. In embodiments, the antibody is administered at an amount from 0.5 nM to 8 nM. In embodiments, the antibody is administered at an amount from 1 nM to 8 nM. In embodiments, the antibody is administered at an amount from 2 nM to 8 nM. In embodiments, the antibody is administered at an amount from 4 nM to 8 nM. In embodiments, the antibody is administered at an amount from 6 nM to 8 nM. In embodiments, the antibody is administered at an amount from 4 nM to 8 nM.

In embodiments, the antibody is administered at an amount from about 0.01 nM to about 6 nM. In embodiments, the antibody is administered at an amount from about 0.05 nM to about 6 nM. In embodiments, the antibody is administered at an amount from about 0.1 nM to about 6 nM. In embodiments, the antibody is administered at an amount from about 0.5 nM to about 8 nM. In embodiments, the antibody is administered at an amount from about 1 nM to about 6 nM. In embodiments, the antibody is administered at an amount from about 2 nM to about 6 nM. In embodiments, the antibody is administered at an amount from about 4 nM to about 6 nM.

In embodiments, the antibody is administered at an amount from 0.01 nM to 6 nM. In embodiments, the antibody is administered at an amount from 0.05 nM to 6 nM. In embodiments, the antibody is administered at an amount from 0.1 nM to 6 nM. In embodiments, the antibody is administered at an amount from 0.5 nM to 6 nM. In embodiments, the antibody is administered at an amount from 1 nM to 6 nM. In embodiments, the antibody is administered at an amount from 2 nM to 6 nM. In embodiments, the antibody is administered at an amount from 4 nM to 6 nM.

In embodiments, the antibody is administered at an amount from about 0.01 nM to about 4 nM. In embodiments, the antibody is administered at an amount from about 0.05 nM to about 4 nM. In embodiments, the antibody is administered at an amount from about 0.1 nM to about 4 nM. In embodiments, the antibody is administered at an amount from about 0.5 nM to about 4 nM. In embodiments, the antibody is administered at an amount from about 1 nM to about 4 nM. In embodiments, the antibody is administered at an amount from about 2 nM to about 4 nM.

In embodiments, the antibody is administered at an amount from 0.01 nM to 4 nM. In embodiments, the antibody is administered at an amount from 0.05 nM to 4 nM. In embodiments, the antibody is administered at an amount from 0.1 nM to 4 nM. In embodiments, the antibody is administered at an amount from 0.5 nM to 4 nM. In embodiments, the antibody is administered at an amount from 1 nM to 4 nM. In embodiments, the antibody is administered at an amount from 2 nM to 4 nM.

In embodiments, the antibody is administered at an amount from about 0.01 nM to about 2 nM. In embodiments, the antibody is administered at an amount from about 0.05 nM to about 2 nM. In embodiments, the antibody is administered at an amount from about 0.1 nM to about 2 nM. In embodiments, the antibody is administered at an amount from about 0.5 nM to about 2 nM. In embodiments, the antibody is administered at an amount from about 1 nM to about 2 nM.

In embodiments, the antibody is administered at an amount from 0.01 nM to 2 nM. In embodiments, the antibody is administered at an amount from 0.05 nM to 2 nM. In embodiments, the antibody is administered at an amount from 0.1 nM to 2 nM. In embodiments, the antibody is administered at an amount from 0.5 nM to 2 nM. In embodiments, the antibody is administered at an amount from 1 nM to 2 nM.

In embodiments, the antibody is administered at an amount from about 0.01 nM to about 1 nM. In embodiments, the antibody is administered at an amount from about 0.05 nM to about 1 nM. In embodiments, the antibody is administered at an amount from about 0.1 nM to about 1 nM. In embodiments, the antibody is administered at an amount from about 0.5 nM to about 1 nM.

In embodiments, the antibody is administered at an amount from 0.01 nM to 1 nM. In embodiments, the antibody is administered at an amount from 0.05 nM to 1 nM. In embodiments, the antibody is administered at an amount from 0.1 nM to 1 nM. In embodiments, the antibody is administered at an amount from 0.5 nM to 1 nM.

In embodiments, the antibody is administered at an amount of about 3.15 nM. In embodiments, the antibody is administered at an amount of 3.15 nM. In embodiments, the antibody is administered at an amount of about 1.05 nM. In embodiments, the antibody is administered at an amount of 1.05 nM.

It is understood that the recombinant protein (i.e., the bispecific antibody or the chimeric antigen receptor) provided herein including embodiments thereof may be administered at any of the concentrations described herein for the administration of the antibody (e.g., 0.01 nM-10 nM).

In embodiments, the antibody is administered at an amount from about 10 μg to about 500 μg. In embodiments, the antibody is administered at an amount from about 20 μg to about 500 μg. In embodiments, the antibody is administered at an amount from about 30 μg to about 500 μg. In embodiments, the antibody is administered at an amount from about 40 μg to about 500 μg. In embodiments, the antibody is administered at an amount from about 50 μg to about 500 μg. In embodiments, the antibody is administered at an amount from about 60 μg to about 500 μg. In embodiments, the antibody is administered at an amount from about 70 μg to about 500 μg. In embodiments, the antibody is administered at an amount from about 80 μg to about 500 μg. In embodiments, the antibody is administered at an amount from about 90 μg to about 500 μg. In embodiments, the antibody is administered at an amount from about 100 μg to about 500 μg.

In embodiments, the antibody is administered at an amount from about 110 μg to about 500 μg. In embodiments, the antibody is administered at an amount from about 120 μg to about 500 μg. In embodiments, the antibody is administered at an amount from about 130 μg to about 500 μg. In embodiments, the antibody is administered at an amount from about 140 μg to about 500 μg. In embodiments, the antibody is administered at an amount from about 150 μg to about 500 μg. In embodiments, the antibody is administered at an amount from about 160 μg to about 500 μg. In embodiments, the antibody is administered at an amount from about 170 μg to about 500 μg. In embodiments, the antibody is administered at an amount from about 180 μg to about 500 μg. In embodiments, the antibody is administered at an amount from about 190 μg to about 500 μg. In embodiments, the antibody is administered at an amount from about 200 μg to about 500 μg.

In embodiments, the antibody is administered at an amount from about 210 μg to about 500 μg. In embodiments, the antibody is administered at an amount from about 220 μg to about 500 μg. In embodiments, the antibody is administered at an amount from about 230 μg to about 500 μg. In embodiments, the antibody is administered at an amount from about 240 μg to about 500 μg. In embodiments, the antibody is administered at an amount from about 250 μg to about 500 μg. In embodiments, the antibody is administered at an amount from about 260 μg to about 500 μg. In embodiments, the antibody is administered at an amount from about 270 μg to about 500 μg. In embodiments, the antibody is administered at an amount from about 280 μg to about 500 μg. In embodiments, the antibody is administered at an amount from about 290 μg to about 500 μg. In embodiments, the antibody is administered at an amount from about 300 μg to about 500 μg.

In embodiments, the antibody is administered at an amount from about 310 μg to about 500 μg. In embodiments, the antibody is administered at an amount from about 320 μg to about 500 μg. In embodiments, the antibody is administered at an amount from about 330 μg to about 500 μg. In embodiments, the antibody is administered at an amount from about 340 μg to about 500 μg. In embodiments, the antibody is administered at an amount from about 350 μg to about 500 μg. In embodiments, the antibody is administered at an amount from about 360 μg to about 500 μg. In embodiments, the antibody is administered at an amount from about 370 μg to about 500 μg. In embodiments, the antibody is administered at an amount from about 380 μg to about 500 μg. In embodiments, the antibody is administered at an amount from about 390 μg to about 500 μg. In embodiments, the antibody is administered at an amount from about 400 μg to about 500 μg.

In embodiments, the antibody is administered at an amount from about 410 μg to about 500 μg. In embodiments, the antibody is administered at an amount from about 420 μg to about 500 μg. In embodiments, the antibody is administered at an amount from about 430 μg to about 500 μg. In embodiments, the antibody is administered at an amount from about 440 μg to about 500 μg. In embodiments, the antibody is administered at an amount from about 450 μg to about 500 μg. In embodiments, the antibody is administered at an amount from about 460 μg to about 500 μg. In embodiments, the antibody is administered at an amount from about 470 μg to about 500 μg. In embodiments, the antibody is administered at an amount from about 480 μg to about 500 μg. In embodiments, the antibody is administered at an amount from about 490 μg to about 500 μg.

In embodiments, the antibody is administered at an amount from about 10 μg to about 400 μg. In embodiments, the antibody is administered at an amount from about 20 μg to about 400 μg. In embodiments, the antibody is administered at an amount from about 30 μg to about 400 μg. In embodiments, the antibody is administered at an amount from about 40 μg to about 400 μg. In embodiments, the antibody is administered at an amount from about 50 μg to about 400 μg. In embodiments, the antibody is administered at an amount from about 60 μg to about 400 μg. In embodiments, the antibody is administered at an amount from about 70 μg to about 400 μg. In embodiments, the antibody is administered at an amount from about 80 μg to about 400 μg. In embodiments, the antibody is administered at an amount from about 90 μg to about 400 μg. In embodiments, the antibody is administered at an amount from about 100 μg to about 400 μg.

In embodiments, the antibody is administered at an amount from about 10 μg to about 300 μg. In embodiments, the antibody is administered at an amount from about 20 μg to about 300 μg. In embodiments, the antibody is administered at an amount from about 30 μg to about 300 μg. In embodiments, the antibody is administered at an amount from about 40 μg to about 300 μg. In embodiments, the antibody is administered at an amount from about 50 μg to about 300 μg. In embodiments, the antibody is administered at an amount from about 60 μg to about 300 μg. In embodiments, the antibody is administered at an amount from about 70 μg to about 300 μg. In embodiments, the antibody is administered at an amount from about 80 μg to about 300 μg. In embodiments, the antibody is administered at an amount from about 90 μg to about 300 μg. In embodiments, the antibody is administered at an amount from about 100 μg to about 300 μg.

In embodiments, the antibody is administered at an amount from about 10 μg to about 200 μg. In embodiments, the antibody is administered at an amount from about 20 μg to about 200 μg. In embodiments, the antibody is administered at an amount from about 30 μg to about 200 μg. In embodiments, the antibody is administered at an amount from about 40 μg to about 200 μg. In embodiments, the antibody is administered at an amount from about 50 μg to about 200 μg. In embodiments, the antibody is administered at an amount from about 60 μg to about 200 μg. In embodiments, the antibody is administered at an amount from about 70 μg to about 200 μg. In embodiments, the antibody is administered at an amount from about 80 μg to about 200 μg. In embodiments, the antibody is administered at an amount from about 90 μg to about 200 μg. In embodiments, the antibody is administered at an amount from about 100 μg to about 200 μg.

In embodiments, the antibody is administered at an amount from about 10 μg to about 100 μg. In embodiments, the antibody is administered at an amount from about 20 μg to about 100 μg. In embodiments, the antibody is administered at an amount from about 30 μg to about 100 μg. In embodiments, the antibody is administered at an amount from about 40 μg to about 100 μg. In embodiments, the antibody is administered at an amount from about 50 μg to about 100 μg. In embodiments, the antibody is administered at an amount from about 60 μg to about 100 μg. In embodiments, the antibody is administered at an amount from about 70 μg to about 100 μg. In embodiments, the antibody is administered at an amount from about 80 μg to about 100 μg. In embodiments, the antibody is administered at an amount from about 90 μg to about 100 μg.

In embodiments, the antibody is administered at an amount of about 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390 μg, 400 μg, 410 μg, 420 μg, 430 μg, 440 μg, 450 μg, 460 μg, 470 μg, 480 μg, 490 μg, or 500 μg.

In embodiments, the antibody is administered at an amount of 10 μg, 20 μg, 30 μg, 40 μg, 50 μg, 60 μg, 70 μg, 80 μg, 90 μg, 100 μg, 110 μg, 120 μg, 130 μg, 140 μg, 150 μg, 160 μg, 170 μg, 180 μg, 190 μg, 200 μg, 210 μg, 220 μg, 230 μg, 240 μg, 250 μg, 260 μg, 270 μg, 280 μg, 290 μg, 300 μg, 310 μg, 320 μg, 330 μg, 340 μg, 350 μg, 360 μg, 370 μg, 380 μg, 390 μg, 400 μg, 410 μg, 420 μg, 430 μg, 440 μg, 450 μg, 460 μg, 470 μg, 480 μg, 490 μg, or 500 μg.

It is understood that the recombinant protein (i.e., the bispecific antibody or the chimeric antigen receptor) provided herein including embodiments thereof may be administered at any of the concentrations described herein for the administration of the antibody (e.g., 10 μg-500 μg).

In embodiments, the recombinant protein or antibody is administered at an amount of about 200 μg. In embodiments, the recombinant protein or antibody is administered at an amount of 200 μg.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Our published and unpublished data showed that CD5 activates STAT3 in both tumor-associated B and T cells, leading to immune-suppression. Blocking CD5 in tumor-associated T or CD5 negative B cells greatly boost antitumor immune responses (FIGS. 1A-1C and FIG. 2C). When compared directly, CD5 and PD1 expression mediates the tumor CD8$^+$ T cell inhibition and blocking CD5 by multiple approaches has stronger immunostimulatory effects than PD-1 antibody in mouse immune system (FIGS. 2A-2E).

Figure 3A:
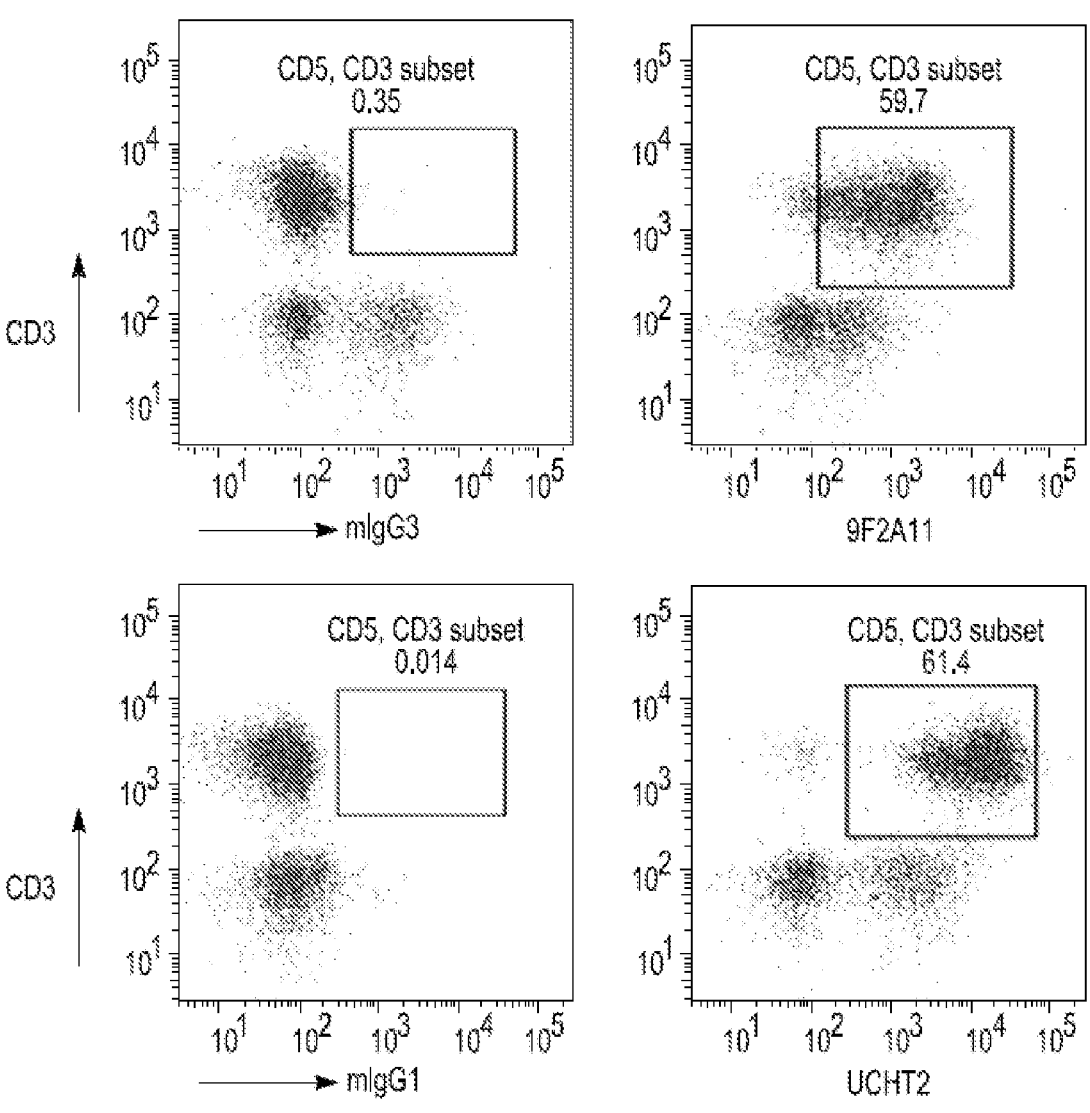
FIGS. 3A-3B present illustrative data showing binding properties of 9F2A11.
Figure 3B:
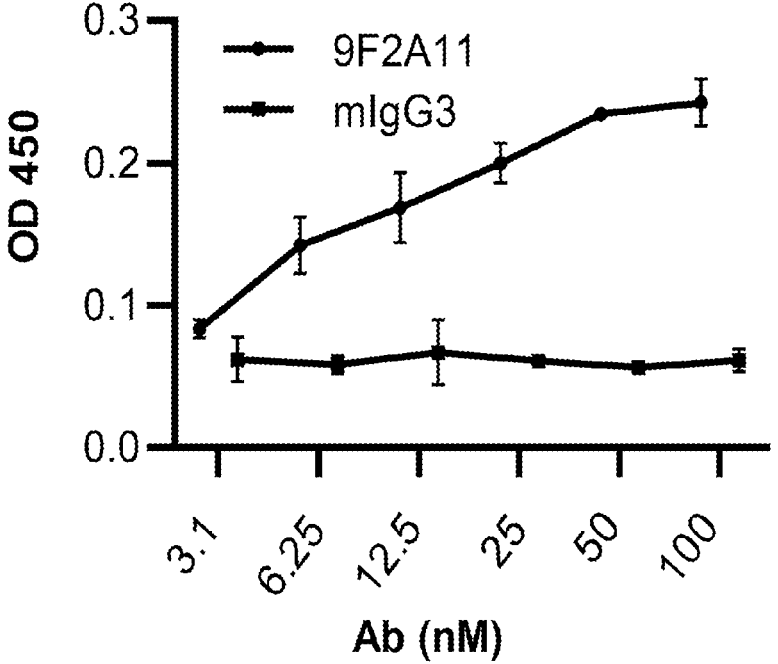
Figure 4A:
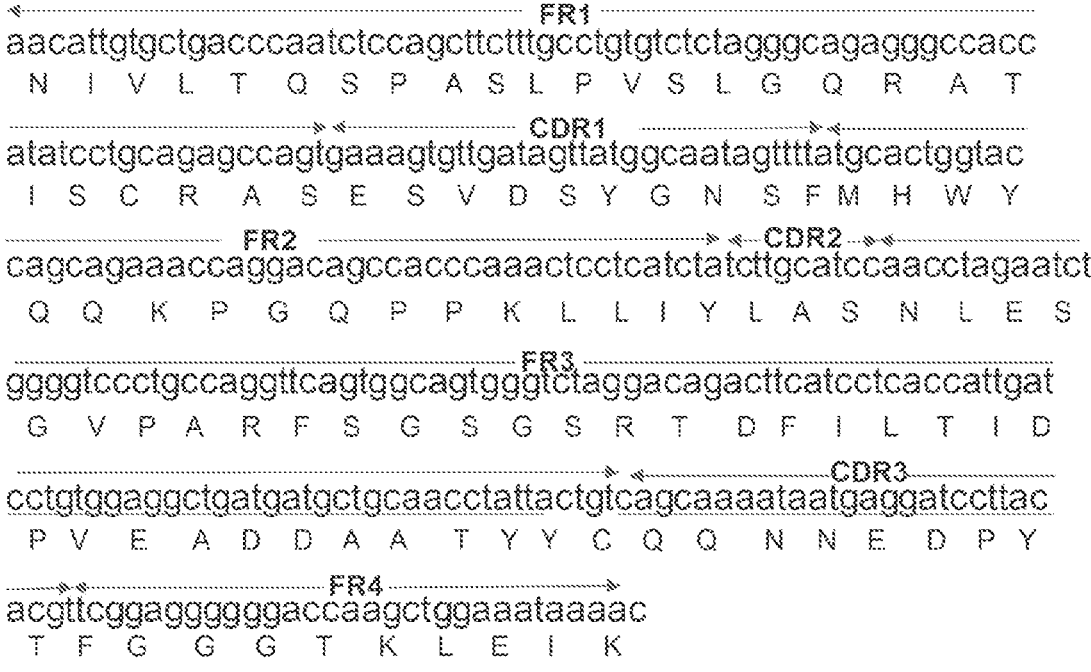
FIGS. 4A-4B present nucleic acid and amino acid sequences of 9F2A11 antibody light-chain and heavy-chain variable gene regions.
Figure 4B:
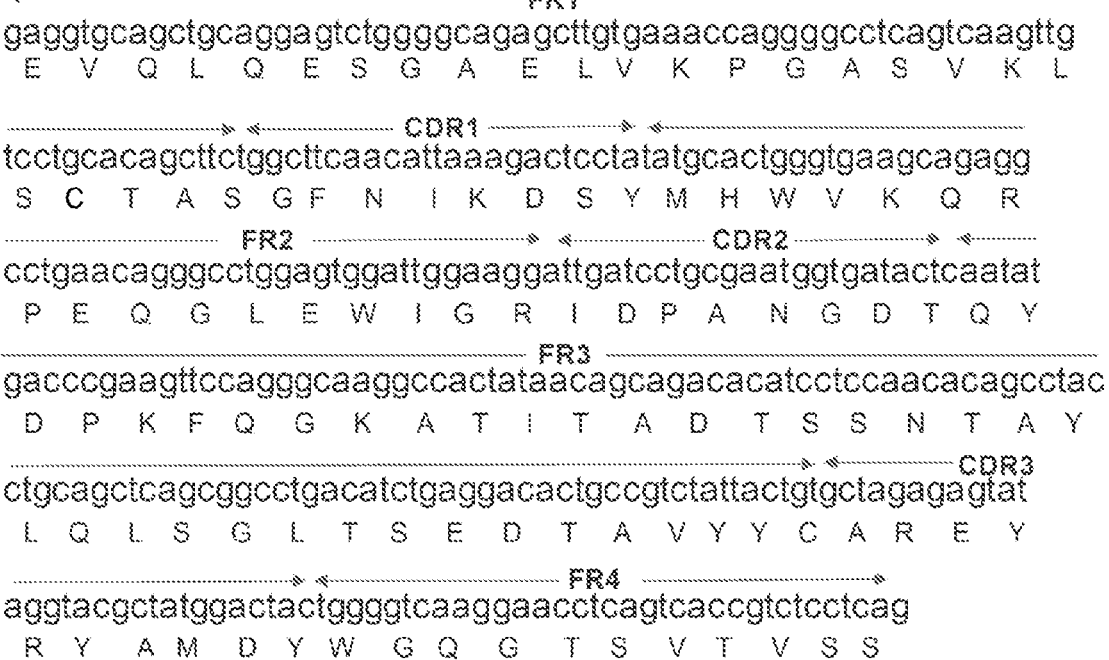

We have now developed a novel anti-human CD5 monoclonal antibody (9F2A11) (FIGS. 3A-3B). We have sequenced the monoclonal antibody, and it is unique and thus novel (FIGS. 4A-4B).

Figure 5:
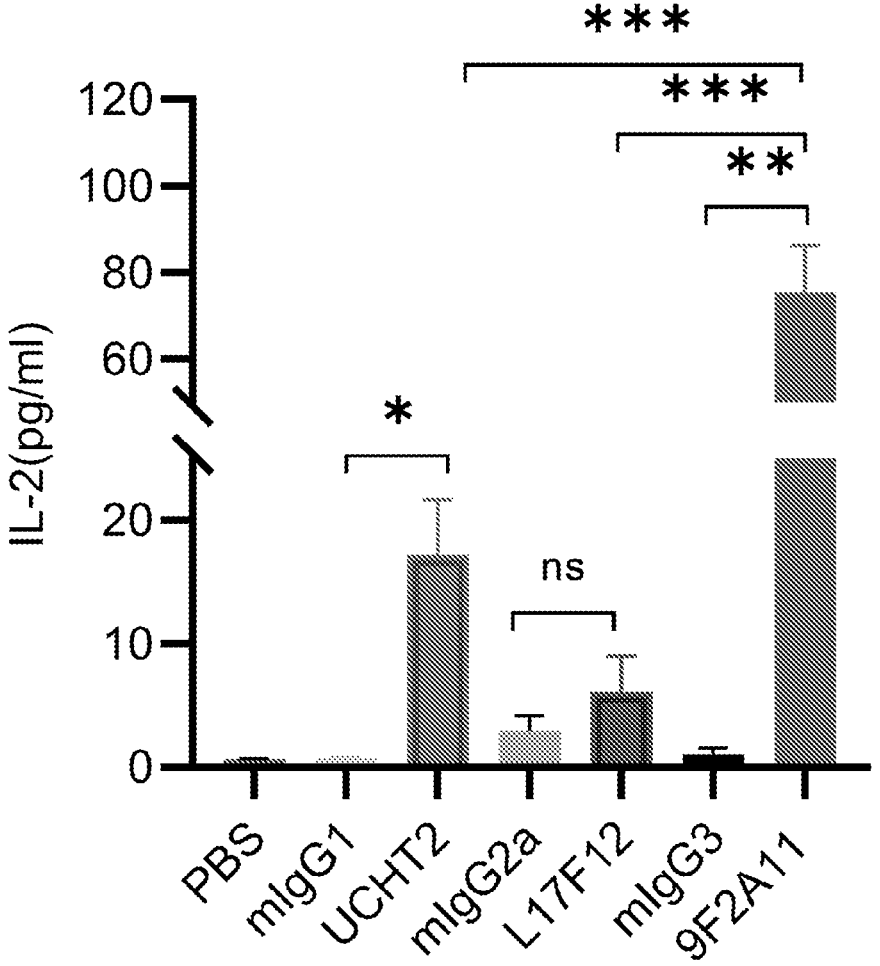
FIG. 5 is a bar graph showing CD5-blocking antibody (9F2A11) increase IL-2 secretion over isotype control, αPD1, UCHT2 (commercially available through, for example, Biolegend) and L17F12 (αCD5, commercially available through, for example, Biolegend). 2×10$^5$ Human PBMC were cultured in the present of isotype control or antibody as indicated for 72 h. IL-2 production were determined in supernatant from cultured medium by ELISA.
Figure 6A:
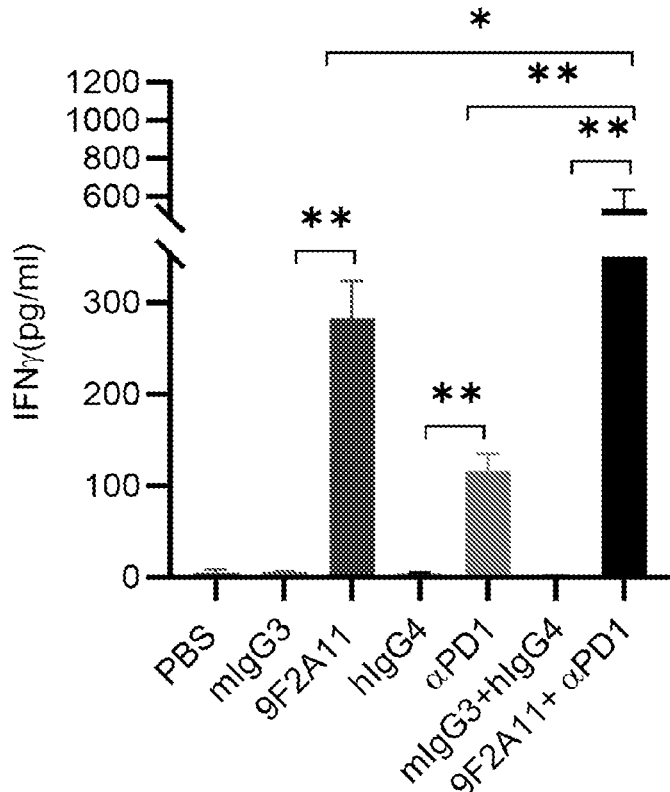
FIG. 6A-B CD5-blocking antibody (9F2A11) increases IFNγ and GZMB production by human CD8+ T cells. (A-B) Human CD8+ T cells from human PBMC were isolated by positive selection with anti-CD8 antibody. Human CD8+ T cells were activated by anti-CD3/CD28 for 2 days, the activated human CD8+ T cells were co-cultured with tumor cells (BxPC3) in the presence of isotype control or antibody as indicated for 48 h. IFN-γ (A) and Granzyme B (B) production were determined in supernatant from co-cultured medium by ELISA.
Figure 6B:
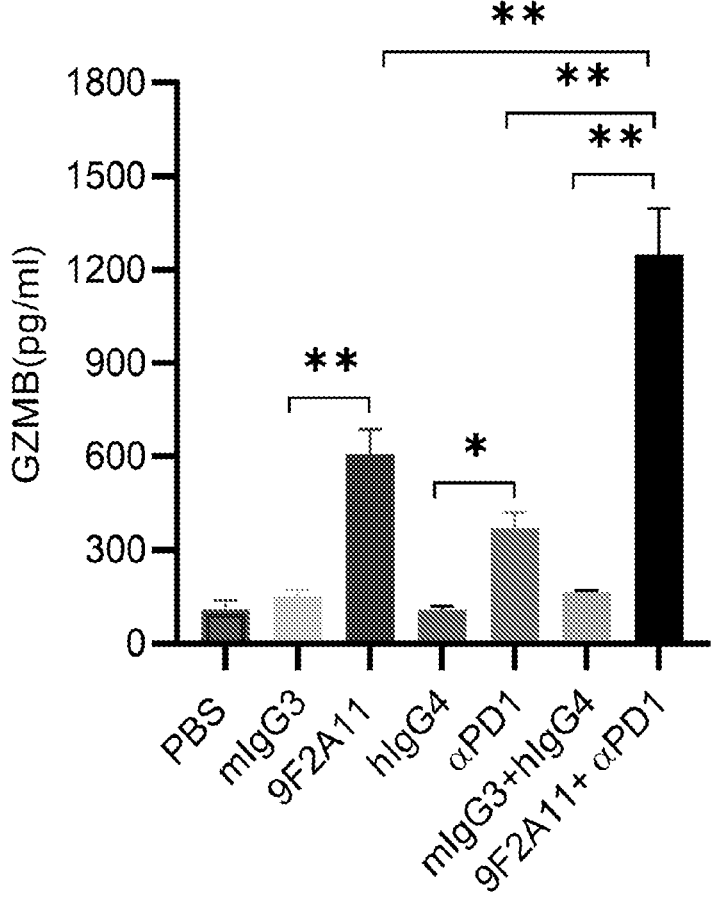
Figure 7A:
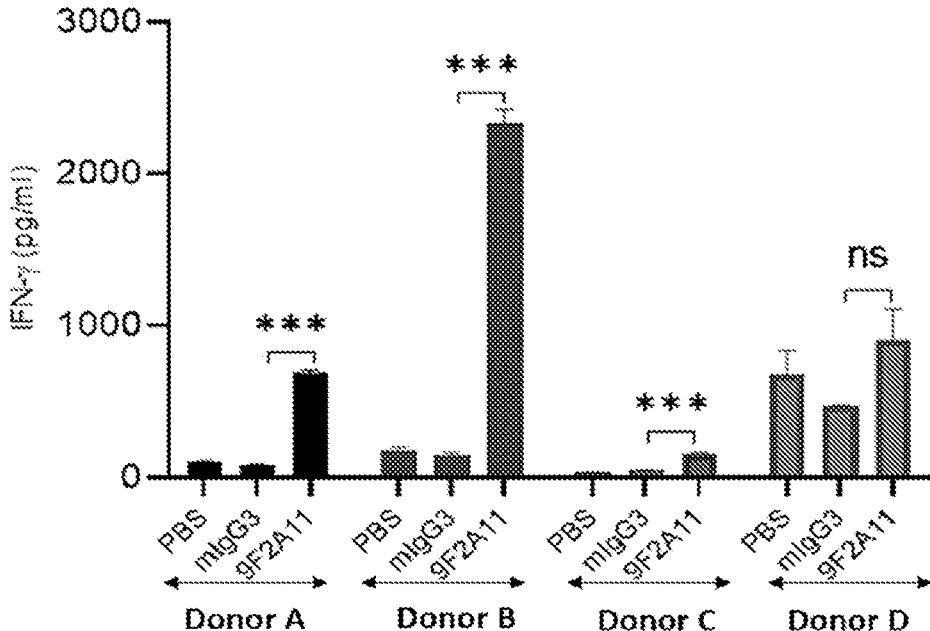
FIG. 7A-B CD5-blocking antibody (9F2A11) increases IFNγ and GZMB production by human CD8+ T cells. (A-B) Human CD8+ T cells from human PBMC were isolated by positive selection with anti-CD8 antibody. Human CD8+ T cells were activated by anti-CD3/CD28 for 2 days, the activated human CD8+ T cells were co-cultured with tumor cells (BxPC3) in the presence of isotype control or antibody as indicated for 48 h. IFN-γ (A) and Granzyme B (B) production were determined in supernatant from co-cultured medium by ELISA. Histogram panels from left to right correspond to donor A, donor B, donor C and donor D.
Figure 7B:
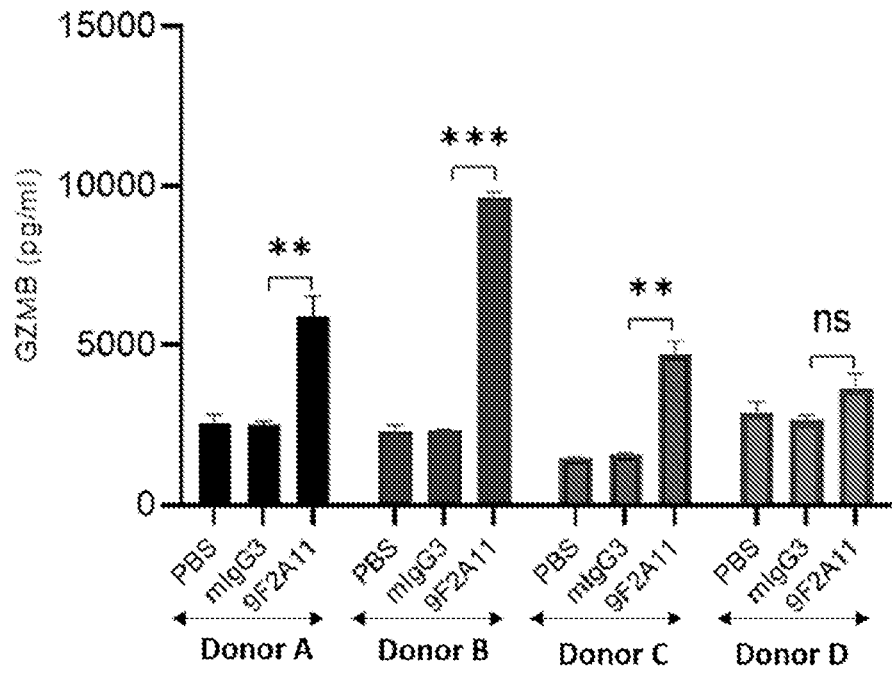
Figure 8:
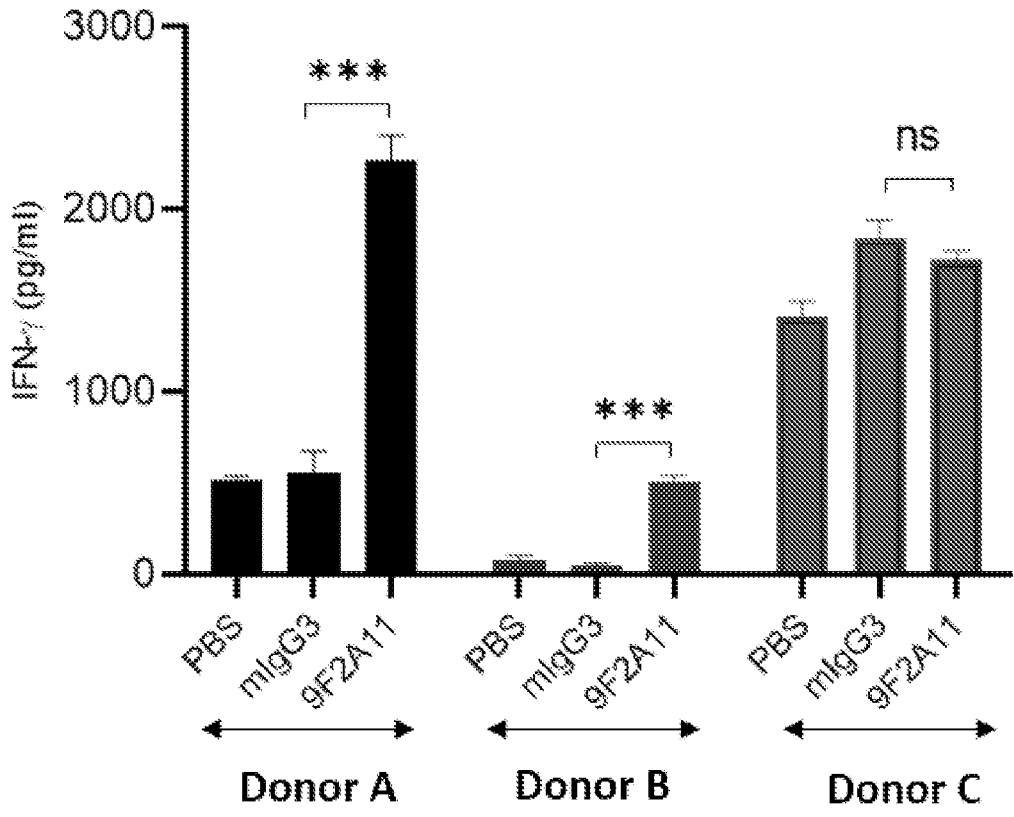
FIG. 8 CD5-blocking antibody (9F2A11) enhances IFNγ production by human CD4+ T cells. Purified human CD4+ T cells were co-cultured with allogeneic monocyte derived DCs in the presence of 9F2A11 antibody or isotype control antibody for 3 days. IFNγ production were determined in supernatant from co-cultured medium by ELISA. Histogram panels from left to right correspond to donor A, donor B, and donor C.
Figure 9:
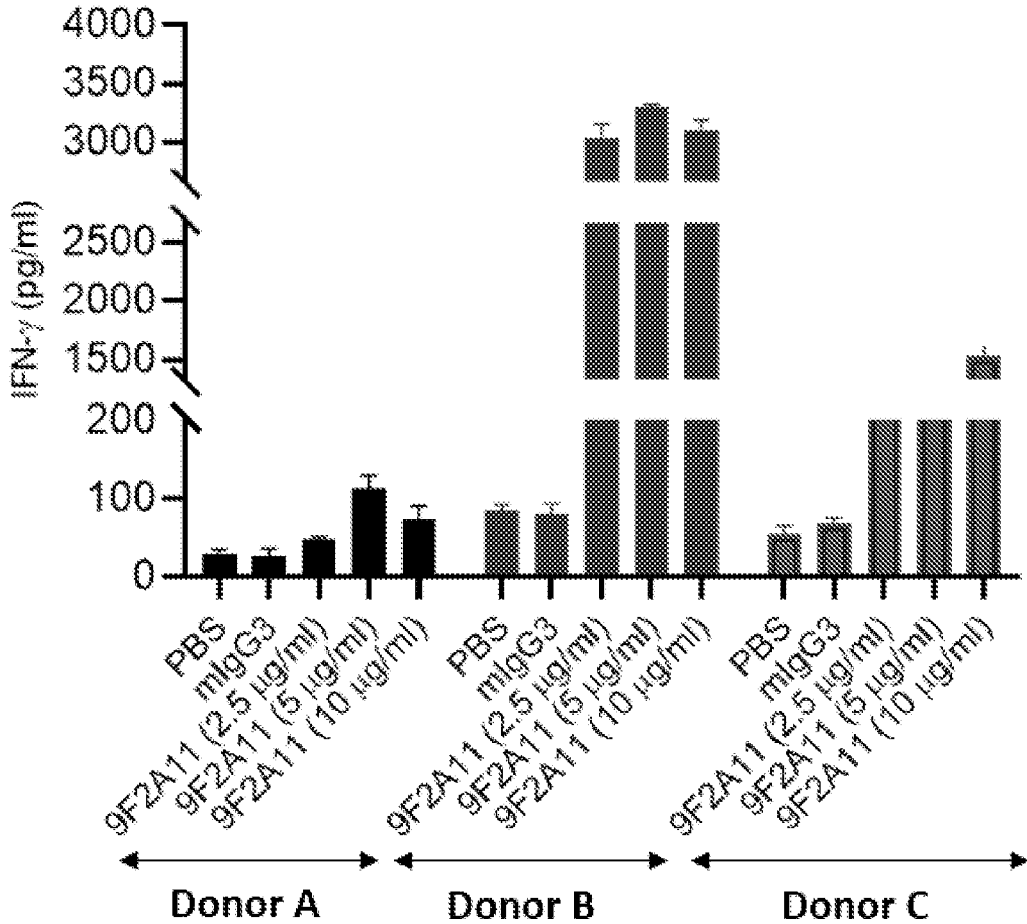
FIG. 9 CD5-blocking antibody (9F2A11) increase IFNγ secretion by human PBMC. 2×105 Human PBMC were cultured in the present of isotype control or antibody as indicated for 72 h. IFNγ production were determined in supernatant from cultured medium by ELISA. Histogram panels from left to right correspond to donor A, donor B, and donor C.

This novel anti-human CD5 antibody is capable of eliciting potent human T cell activities (FIG. 5). The capacity of the monoclonal CD5 antibody in inducing human T cell activation is superior than commercial CD5 antibody under the experimental conditions (FIG. 4). In addition, when the monoclonal CD5 antibody is used in combination with a clinical PD-1 antibody, a synergy in human T cell activation is detected (FIGS. 6A-6B). In addition, the capacity of the monoclonal CD5 (9F2A11) in inducing human T cell activation is superior than PD1 antibody (FIGS. 6A-6B).

P EMBODIMENTS

P Embodiment 1. An anti-CD5 antibody comprising a light chain variable domain and a heavy chain variable domain, wherein said light chain variable domain comprises:
a CDR L1 as set forth in SEQ ID NO:1, a CDR L2 as set forth in SEQ ID NO:2 and a CDR L3 as set forth in SEQ ID NO:3; and
wherein said heavy chain variable domain comprises:
a CDR H1 as set forth in SEQ ID NO:4, a CDR H2 as set forth in SEQ ID NO:5, and a CDR H3 as set forth in SEQ ID NO:6.

P Embodiment 2. The antibody of P embodiment 1, wherein said light chain variable domain comprises a FR L1 as set forth in SEQ ID NO:7, a FR L2 as set forth in SEQ ID NO:8, a FR L3 as set forth in SEQ ID NO:9 and a FR L4 as set forth in SEQ ID NO:10.

P Embodiment 3. The antibody of P embodiment 1 or 2, wherein said heavy chain variable domain comprises a FR H1 as set forth in SEQ ID NO:11, a FR H2 as set forth in SEQ ID NO:12, a FR H3 as set forth in SEQ ID NO:13 and a FR H4 as set forth in SEQ ID NO:14.

P Embodiment 4. The antibody of any one of P embodiments 1-3, wherein said light chain variable domain comprises the sequence of SEQ ID NO:15.

P Embodiment 5. The antibody of any one of P embodiments 1-4, wherein said heavy chain variable domain comprises the sequence of SEQ ID NO:16.

P Embodiment 6. The antibody of any one of P embodiments 1-7, wherein said antibody is a humanized antibody.

P Embodiment 7. The antibody of any one of P embodiments 1-5, wherein said antibody is a chimeric antibody.

P Embodiment 8. The antibody of any one of P embodiments 1-5, wherein said antibody is a Fab' fragment.

P Embodiment 9. The antibody of any one of P embodiments 1-6, wherein said antibody is a single chain antibody (scFv).

P Embodiment 10. The antibody of any one of P embodiments 1-5 or 9, wherein said light chain variable domain and said heavy chain variable domain form part of a scFv P Embodiment 11. The antibody of any one of P embodiments 1-7, wherein said antibody is an IgG.

P Embodiment 12. The antibody of any one of P embodiments 1-7, wherein said antibody is an IgG1.

P Embodiment 13. The antibody of any one of P embodiments 1-12, wherein said antibody is capable of binding CD5.

P Embodiment 14. The antibody of any one of P embodiments 1-13, wherein said antibody is bound to CD5.

P Embodiment 15. The antibody of P embodiment 14, wherein said CD5 forms part of a cell.

P Embodiment 16. The antibody of P embodiment 15, wherein said cell is a lymphoid cell.

P Embodiment 17. The antibody of P embodiment 15 or 16, wherein said cell is a B cell or a T cell.

P Embodiment 18. An isolated nucleic acid encoding an antibody of P embodiment 1.

P Embodiment 19. A pharmaceutical composition comprising a therapeutically effective amount of an antibody of any one of P embodiments 1-17 and a pharmaceutically acceptable excipient.

P Embodiment 20. The pharmaceutical composition of P embodiment 19, further comprising a therapeutically effective amount of a Programmed Death 1 (PD-1) inhibitor.

P Embodiment 21. The pharmaceutical composition of P embodiment 19 or 20, wherein said PD-1 inhibitor is Nivolumab, Pembrolizumab, or Cemiplimab.

P Embodiment 22. The pharmaceutical composition of any one of P embodiments 19-21, wherein said therapeutically effective amount of said antibody and said therapeutically effective amount of said PD-1 inhibitor is a combined synergistic amount.

P Embodiment 23. A method of treating cancer in a subject in need thereof, said method comprising administering to a subject a therapeutically effective amount of an antibody of any one of P embodiments 1-17, thereby treating cancer in said subject.

P Embodiment 24. The method of P embodiment 23, further comprising administering a therapeutically effective amount of a PD-1 inhibitor.

P Embodiment 25. The method of P embodiment 24, wherein the effective amount of an antibody and the effective amount of a PD-1 inhibitor are a combined synergistic amount.

P Embodiment 26. The method of P embodiment 24 or 25, wherein said antibody and said PD-1 inhibitor are administered sequentially or concurrently.

P Embodiment 27. The method of any one of P embodiments 24-26, wherein said antibody and said PD-1 inhibitor are admixed together prior to administration.

P Embodiment 28. The method of any one of P embodiments 24-27, wherein said antibody and said PD-1 inhibitor are administered in a single dosage form.

P Embodiment 29. The method of any one of P embodiments 24-26, wherein said antibody and said PD-1 inhibitor are administered in two separate dosage forms.

P Embodiment 30. A method of treating cancer in a subject in need thereof, said method comprising administering to a subject a combined effective amount of an antibody of any one of P embodiments 1-17 and a PD-1 inhibitor, thereby treating cancer in said subject.

P Embodiment 31. The method of P embodiment 30, wherein the combined effective amount is a combined synergistic amount.

P Embodiment 32. A recombinant protein comprising:

(i) an antibody region comprising:

(a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6; and (ii) a transmembrane domain.

P Embodiment 33. An isolated nucleic acid encoding a recombinant protein of P embodiment 32.

P Embodiment 34. A pharmaceutical composition comprising a therapeutically effective amount of a recombinant protein of P embodiment 32 and a pharmaceutically acceptable excipient.

P Embodiment 35. A method of treating cancer in a subject in need thereof, said method comprising administering to a subject a therapeutically effective amount of a recombinant protein of P embodiment 32, thereby treating cancer in said subject.

P Embodiment 36. The method of P embodiment 35, further comprising administering a therapeutically effective amount of a PD-1 inhibitor.

P Embodiment 37. A recombinant protein comprising:

(i) a first antibody region capable of binding an effector cell ligand; and (ii) a second antibody region, comprising:

(a) a light chain variable domain comprising a CDR L1 as set forth in SEQ ID NO:1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6.

P Embodiment 38. A pharmaceutical composition comprising a therapeutically effective amount of a recombinant protein of P embodiment 37 and a pharmaceutically acceptable excipient.

P Embodiment 39. A method of treating cancer in a subject in need thereof, said method comprising administering to a subject a therapeutically effective amount of a recombinant protein of P embodiment 37, thereby treating cancer in said subject.

INFORMAL SEQUENCE LISTING:
Light chain CDRL1 amino acid sequence
(SEQ ID NO: 1):
ESVDSYGNSF Light chain CDRL2 amino acid sequence
(SEQ ID NO: 2):
LAS -continued
Light chain CDRL3 amino acid sequence
(SEQ ID NO: 3):
QQNNEDPYT Heavy chain CDRH1 amino acid sequence
(SEQ ID NO: 4):
GFNIKDSY Heavy chain CDRH2 amino acid sequence
(SEQ ID NO: 5):
IDPANGDT Heavy chain CDRH3 amino acid sequence
(SEQ ID NO: 6):
AREYRYAMDY Light chain FRL1 amino acid sequence
(SEQ ID NO: 7):
NIVLTQSPASLPVSLGQRATISCRAS Light chain FRL2 amino acid sequence
(SEQ ID NO: 8):
MHWYQQKPGQPPKLLIY Light chain FRL3 amino acid sequence
(SEQ ID NO: 9):
NLESGVPARFSGSGSRTDFILTIDPVEADDAATYYC Light chain FRL4 amino acid sequence
(SEQ ID NO: 10):
FGGGTKLEIK Heavy chain FRH1 amino acid sequence
(SEQ ID NO: 11):
EVQLQESGAELVKPGASVKLSCTAS Heavy chain FRH2 amino acid sequence
(SEQ ID NO: 12):
MHWVKQRPEQGLEWIGR Heavy chain FRH3 amino acid sequence
(SEQ ID NO: 13):
QYDPKFQGKATITADTSSNTAYLQLSGLTSEDTAVYYC Heavy chain FRH4 amino acid sequence
(SEQ ID NO: 14):
WGQGTSVTVSS Light chain full amino acid sequence
(SEQ ID NO: 15):
NIVLTQSPASLPVSLGQRATISCRASESVDSYGNSFMHWYQQKPGQPPKL

LIYLASNLESGVPARFSGSGSRTDFILTIDPVEADDAATYYCQQNNEDPY

TFGGGTKLEIK

Heavy chain full amino acid sequence
(SEQ ID NO: 16):
EVQLQESGAELVKPGASVKLSCTASGFNIKDSYMHWVKQRPEQGLEWIGR

IDPANGDTQYDPKFQGKATITADTSSNTAYLQLSGLTSEDTAVYYCAREY

RYAMDYWGQGTSVTVSS

Light chain CDRL1 DNA sequence
(SEQ ID NO: 17):
gaaagtgttgatagttatggcaatagtttt

Light chain CDRL2 DNA sequence
(SEQ ID NO: 18):
cttgcatcc

Light chain CDRL3 DNA sequence
(SEQ ID NO: 19):
cagcaaaataatgaggatccttacacg

Heavy chain CDRH1 DNA sequence
(SEQ ID NO: 20):
ggcttcaacattaaagactcctat

-continued

Heavy chain CDRH2 DNA sequence
(SEQ ID NO: 21):
attgatcctgcgaatggtgatact

Heavy chain CDRH3 DNA sequence
(SEQ ID NO:22):
gctagagagtataggtacgctatggactac

Light chain FRL1 DNA sequence
(SEQ ID NO: 23):
aacattgtgctgacccaatctccagcttctttgcctgtgtctctagggca gagggccaccatatcctgcagagccagt Light chain FRL2 DNA sequence
(SEQ ID NO: 24):
atgcactggtaccagcagaaaccaggacagccacccaaactcctcatcta t Light chain FRL3 DNA sequence(SEQ ID NO: 25):
aacctagaatctggggtccctgccaggttcagtggcagtgggtctaggac agacttcatcctcaccattgatcctgtggaggctgatgatgctgcaacct attactgt Light chain FRL4 DNA sequence
(SEQ ID NO: 26):
ttcggaggggggaccaagctggaaataaaac Heavy chain FRH1 DNA sequence
(SEQ ID NO: 27):
gaggtgcagctgcaggagtctggggcagagcttgtgaaaccagggggcctc agtcaagttgtcctgcacagcttct Heavy chain FRH2 DNA sequence
(SEQ ID NO: 28):
atgcactgggtgaagcagaggcctgaacagggcctggagtggattggaag g -continued Heavy chain FRH3 DNA sequence
(SEQ ID NO: 29):
caatatgacccgaagttccagggcaaggccactataacagcagacacatc ctccaacacagcctacctgcagctcagcggcctgacatctgaggacactg ccgtctattactgt Heavy chain FRH4 DNA sequence
(SEQ ID NO: 30):
tggggtcaaggaacctcagtcaccgtctcctcag Light chain full DNA sequence
(SEQ ID NO: 31):
aacattgtgctgacccaatctccagcttctttgcctgtgtctctagggca gagggccaccatatcctgcagagccagtgaaagtgttgatagttatggca atagtttttatgcactggtaccagcagaaaccaggacagccacccaaactc ctcatctatcttgcatccaacctagaatctggggtccctgccaggttcag tggcagtgggtctaggacagacttcatcctcaccattgatcctgtggagg ctgatgatgctgcaacctattactgtcagcaaaataatgaggatccttac acgttcggaggggggaccaagctggaaataaaac Heavy chain full DNA sequence
(SEQ ID NO: 32):
gaggtgcagctgcaggagtctggggcagagcttgtgaaaccagggggcctc agtcaagttgtcctgcacagcttctggcttcaacattaaagactcctata tgcactgggtgaagcagaggcctgaacagggcctggagtggattggaagg attgatcctgcgaatggtgatactcaatatgacccgaagttccagggcaa ggccactataacagcagacacatcctccaacacagcctacctgcagctca gcggcctgacatctgaggacactgccgtctattactgtgctagagagtat aggtacgctatggactactggggtcaaggaacctcagtcaccgtctcctc ag

---

What is claimed is:

1. An anti-CD5 antibody comprising a light chain variable domain and a heavy chain variable domain, wherein said light chain variable domain comprises:

a CDR L1 as set forth in SEQ ID NO:1, a CDR L2 as set forth in SEQ ID NO: 2 and a CDR L3 as set forth in SEQ ID NO:3; and wherein said heavy chain variable domain comprises:

a CDR H1 as set forth in SEQ ID NO:4, a CDR H2 as set forth in SEQ ID NO: 5, and a CDR H3 as set forth in SEQ ID NO:6.

2. The antibody of claim 1, wherein said light chain variable domain comprises the sequence of SEQ ID NO:15.

3. The antibody of claim 1, wherein said heavy chain variable domain comprises the sequence of SEQ ID NO:16.

4. The antibody of claim 1, wherein said antibody is bound to CD5.

5. The antibody of claim 4, wherein said CD5 forms part of a cell.

6. A recombinant protein comprising:

(i) an antibody region comprising:

(a) a light chain variable domain comprising a CDR L1 as set forth in SEQ ID NO: 1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6; and (ii) a transmembrane domain.

7. A recombinant protein comprising:

(i) a first antibody region capable of binding an effector cell ligand; and (ii) a second antibody region, comprising:

(a) a light chain variable domain comprising a CDR L1 as set forth in SEQ ID NO: 1, a CDR L2 as set forth in SEQ ID NO:2 and a CDR L3 as set forth in SEQ ID NO:3; and (b) a heavy chain variable domain a CDR H1 as set forth in SEQ ID NO:4, a CDR H2 as set forth in SEQ ID NO:5, and a CDR H3 as set forth in SEQ ID NO:6.

8. An isolated nucleic acid encoding an antibody of claim 1.

9. An isolated nucleic acid encoding a recombinant protein of claim 6.

10. A pharmaceutical composition comprising a therapeutically effective amount of an antibody of claim 1 and a pharmaceutically acceptable excipient.

11. The pharmaceutical composition of claim 10, further comprising a therapeutically effective amount of a Programmed Death 1 (PD-1) inhibitor.

12. A pharmaceutical composition comprising a therapeutically effective amount of a recombinant protein of claim 6 and a pharmaceutically acceptable excipient.

13. A pharmaceutical composition comprising a therapeutically effective amount of a recombinant protein of claim 7 and a pharmaceutically acceptable excipient.

14. A method of treating cancer in a subject in need thereof, said method comprising administering to a subject a therapeutically effective amount of an antibody of claim 1, thereby treating cancer in said subject.

15. The method of claim 14, further comprising administering a therapeutically effective amount of a PD-1 inhibitor.

16. A method of treating cancer in a subject in need thereof, said method comprising administering to a subject a combined effective amount of an antibody of claim 1 and a PD-1 inhibitor, thereby treating cancer in said subject.

17. A method of treating cancer in a subject in need thereof, said method comprising administering to a subject a therapeutically effective amount of a recombinant protein of claim 6, thereby treating cancer in said subject.

18. The method of claim 17, further comprising administering a therapeutically effective amount of a PD-1 inhibitor.

19. A method of treating cancer in a subject in need thereof, said method comprising administering to a subject a therapeutically effective amount of a recombinant protein of claim 7, thereby treating cancer in said subject.

* * * * *